(12) United States Patent
Gerhart et al.

(10) Patent No.: US 10,940,110 B2
(45) Date of Patent: Mar. 9, 2021

(54) METHOD AND SYSTEM FOR THE TREATMENT OF CHRONIC COPD WITH NEBULIZED ANTICHOLINERGIC ADMINISTRATIONS

(71) Applicant: Sunovion Respiratory Development Inc., Marlborough, MA (US)

(72) Inventors: William Gerhart, La Mesa, CA (US); Ahmet Tutuncu, San Diego, CA (US)

(73) Assignee: SUNOVION RESPIRATORY DEVELOPMENT INC., Marlborough, MA (US)

(*) Notice: Subject to any disclaimer, the term of this patent is extended or adjusted under 35 U.S.C. 154(b) by 0 days.

(21) Appl. No.: 16/217,765

(22) Filed: Dec. 12, 2018

(65) Prior Publication Data

US 2019/0254967 A1    Aug. 22, 2019

Related U.S. Application Data

(63) Continuation of application No. 15/050,280, filed on Feb. 22, 2016, now abandoned, which is a continuation of application No. 12/547,406, filed on Aug. 25, 2009, now abandoned, which is a continuation-in-part of application No. 12/393,709, filed on Feb. 26, 2009, now abandoned.

(60) Provisional application No. 61/080,184, filed on Jul. 11, 2008, provisional application No. 61/031,639, filed on Feb. 26, 2008.

(51) Int. Cl.
| | |
|---|---|
| A61K 9/00 | (2006.01) |
| A61K 31/00 | (2006.01) |
| A61K 31/4015 | (2006.01) |
| A61K 31/56 | (2006.01) |
| A61K 31/40 | (2006.01) |
| A61M 11/00 | (2006.01) |

(52) U.S. Cl.
CPC ............ *A61K 9/0078* (2013.01); *A61K 31/00* (2013.01); *A61K 31/40* (2013.01); *A61K 31/4015* (2013.01); *A61K 31/56* (2013.01); *A61M 11/00* (2013.01)

(58) Field of Classification Search
CPC .......................... A61K 31/4015; A61K 9/0078
See application file for complete search history.

(56) References Cited

U.S. PATENT DOCUMENTS

| | | |
|---|---|---|
| 3,480,626 A | 11/1969 | Pfleger et al. |
| 3,994,974 A | 11/1976 | Murakami et al. |
| 4,496,086 A | 1/1985 | Duchadeau |
| 4,992,474 A | 2/1991 | Skidmore et al. |
| 5,152,456 A | 10/1992 | Ross et al. |
| 5,261,601 A | 11/1993 | Ross et al. |
| 5,280,784 A | 1/1994 | Kohler |
| 5,309,900 A | 5/1994 | Knoch et al. |
| 5,312,046 A | 5/1994 | Knoch et al. |
| 5,458,136 A | 10/1995 | Jaser et al. |
| 5,461,695 A | 10/1995 | Knoch |
| 5,518,179 A | 5/1996 | Humberstone et al. |
| 5,544,646 A | 8/1996 | Lloyd et al. |
| 5,549,102 A | 8/1996 | Lintl et al. |
| 5,603,918 A | 2/1997 | McNamara |
| 5,740,966 A | 4/1998 | Blaha-Schnabel |
| 5,795,564 A | 8/1998 | Aberg et al. |
| 5,957,389 A | 9/1999 | Wunderlich et al. |
| 6,000,394 A | 12/1999 | Blaha-Schnabel et al. |
| 6,004,537 A | 12/1999 | Blondino et al. |
| 6,024,940 A | 2/2000 | Ghio et al. |
| 6,040,344 A | 3/2000 | Gao et al. |
| 6,068,833 A | 5/2000 | Aberg et al. |
| 6,085,741 A | 7/2000 | Becker |
| 6,106,479 A | 8/2000 | Wunderlich et al. |
| 6,113,927 A | 9/2000 | Hatakeyama |
| 6,150,418 A | 11/2000 | Hochrainer et al. |
| 6,176,237 B1 | 1/2001 | Wunderlich et al. |
| 6,261,539 B1 | 7/2001 | Adjei et al. |
| 6,433,003 B1 | 8/2002 | Bobrove et al. |
| 6,445,524 B1 | 9/2002 | Nazarian et al. |
| 6,472,563 B1 | 10/2002 | Tanoury et al. |
| 6,513,519 B2 | 2/2003 | Gallem |
| 6,513,727 B1 | 2/2003 | Jaser et al. |
| 6,518,179 B1 | 2/2003 | Joo |
| 6,537,524 B1 | 3/2003 | Hassan et al. |
| 6,598,603 B1 | 7/2003 | Andersson et al. |
| 6,630,466 B2 | 10/2003 | Bozung et al. |
| 6,667,344 B2 | 12/2003 | Banerjee et al. |
| 6,719,994 B2 | 4/2004 | Meoli et al. |
| 6,720,453 B2 | 4/2004 | Tanoury et al. |
| 6,750,226 B2 | 6/2004 | Forner et al. |
| 6,814,953 B2 | 11/2004 | Banerjee et al. |
| 6,866,839 B2 | 3/2005 | Aberg et al. |

(Continued)

FOREIGN PATENT DOCUMENTS

| | | |
|---|---|---|
| EP | 1894559 A1 | 3/2008 |
| WO | WO-01/34232 A1 | 5/2001 |

(Continued)

OTHER PUBLICATIONS

Addis et al., "Assessment of a Combination of Doses of Fenoterol and Ipratropium Suitable for a Single Metered-Dose Aerosol," Eur. J. Clin. Pharmacal. 16:97-100 (1979).

Alex et al., "Glycopyrrolate Inhalation Aerosol in the Treatment of Chronic Obstructive Pulmonary Disease," Am. J. Resp. Crit. Care Med. 149(4):B22 (1994) (Abstract).

Alex et al., "Nebulized Glycopyrrolate Causes Significant and Long-Lasting Bronchodilation in Patients with Chronic Obstructive Pulmonary Disease," Am. J. Resp. Crit. Care Med. 159(3):A823 (1999) (Abstract).

Arvidsson, P. et al., "Formoterol, a new long-acting bronchodilator for inhalation," Eur. Resp. J. 2:325-330 (1989).

(Continued)

*Primary Examiner* — James D. Anderson
(74) *Attorney, Agent, or Firm* — Heslin Rothenberg Farley & Mesiti P.C.

(57) ABSTRACT

A method is provided for improving lung function in COPD by administering a muscarinic antagonist with a high efficiency nebulizer.

18 Claims, 8 Drawing Sheets

(56) References Cited

U.S. PATENT DOCUMENTS

| | | | |
|---|---|---|---|
| 6,887,459 | B1 | 5/2005 | Haeberlin |
| 6,962,151 | B1 | 11/2005 | Knoch et al. |
| 6,983,747 | B2 | 1/2006 | Gallem et al. |
| 7,018,618 | B2 | 3/2006 | Lewis et al. |
| 7,059,320 | B2 | 6/2006 | Feiner et al. |
| 7,208,501 | B2 | 4/2007 | Buil Albero et al. |
| 7,229,607 | B2 | 6/2007 | Bannister et al. |
| 7,252,085 | B2 | 8/2007 | Kunschir |
| 7,291,115 | B2 | 11/2007 | Cardona Burrul |
| 7,312,231 | B2 | 12/2007 | Buil Albero et al. |
| 7,348,362 | B2 | 3/2008 | Banerjee et al. |
| 7,462,645 | B2 | 12/2008 | Chaudry et al. |
| 7,465,756 | B2 | 12/2008 | Chaudry et al. |
| 7,473,710 | B2 | 1/2009 | Chaudry et al. |
| 2003/0124063 | A1 | 7/2003 | Chaudry et al. |
| 2004/0002548 | A1 | 1/2004 | Bozung et al. |
| 2005/0175547 | A1 | 8/2005 | Maus et al. |
| 2005/0175549 | A1 | 8/2005 | Goede et al. |
| 2006/0062738 | A1 | 3/2006 | Hofmann et al. |
| 2006/0120966 | A1 | 6/2006 | Church et al. |
| 2006/0270667 | A1 | 11/2006 | Pieper et al. |
| 2007/0167496 | A1 | 7/2007 | Karl et al. |
| 2007/0191323 | A1 | 8/2007 | Hill et al. |
| 2007/0207091 | A1 | 9/2007 | McAffer et al. |
| 2007/0249572 | A1 | 10/2007 | Hill |
| 2007/0256684 | A1 | 11/2007 | Kelliher et al. |
| 2007/0276048 | A1 | 11/2007 | Deshmukh et al. |
| 2008/0020003 | A1 | 1/2008 | Hill et al. |
| 2008/0020048 | A1 | 1/2008 | Snape et al. |
| 2008/0207736 | A1 | 8/2008 | Ji et al. |
| 2009/0025713 | A1 | 1/2009 | Keller et al. |
| 2009/0215734 | A1 | 8/2009 | Gerhart |

FOREIGN PATENT DOCUMENTS

| | | |
|---|---|---|
| WO | WO-2001/008681 | 8/2001 |
| WO | WO-2004/091536 A2 | 10/2004 |
| WO | WO-2005/105043 A2 | 11/2005 |
| WO | WO-2006/008213 A1 | 1/2006 |
| WO | WO-2006/079841 A1 | 8/2006 |
| WO | WO-2007/057219 A1 | 5/2007 |
| WO | WO-2007/137204 A2 | 11/2007 |

OTHER PUBLICATIONS

AU 2009241628 Examination Report dated Aug. 24, 2011.
Baculard, A., "Place du Bronchodual dans le traitement de fond de l'asthme de 1-enfant," Arch.Pediatr. 2(Suppl. 2):149s-153s (1995).
Barnes, P., "Novel Approaches and Targets for Treatment of Chronic Obstructive Pulmonary Disease," Am. J. Respir. Crit. Care Med. 160(5):S72-S79 (1999).
Bartow and Brogden, "Formoterol. An Update of its Pharmacological Properties and Therapeutic Efficacy in the Management of Asthma," Drugs 55(2):303-322 (1998).
Bauer, K. et al., "Effect of solution and suspension type aerosol of formoterol on tremor response and airways in patients with asthma," J. Allergy Clin Immunol. 96:495-501 ( 1995).
Bianco et al., "Part II. Treatment of Reversible Airway Obstruction with Duovent. Principles and Clinico-Functional Aspects," Respiration 50 (Suppl. 2):137-139 (1986).
Biological Buffers, Sigma Aldrich Apr. 15, 2008, http://www.sigrnaaldrich.com/sigma-aldrich.
British Thoracic Society Nebulizer Project Group, "Nebulizer Therapy. Guidelines," Thorax 1997:52(Suppl 2):SI.
Brovana package insert Jan. 3, 2007.
Bryant, D.H. et al., "Oxitropium Bromide: An Acute Dose Response Study of a New Anticholinergic Drug in Combination with Fenoterol in Asthma and Chronic Bronchitis," Pulmonary Pharmacology (1990) 3:55-58.
CA 2,716,936 Examination Report dated Jan. 3, 2012.
Canadian Examiners Report issued by the Canadian Intellectual Property Office for Application No. 2,716,936 dated Aug. 21, 2013 (3 pages).
Canadian Examiners Report issued by the Canadian Intellectual Property Office for Application No. 2,716,936 dated Oct. 31, 2012 (3 pages).
Cazzola, M. et al., "Incremental Benefit of Adding Oxitropium Bromide to Formoterol in Patients with Stable COPD," Pulmonary Pharmacal. Ther. 12:267-271 (1999).
Combivent Inhalation Aerosol Study Group, "In chronic obstructive pulmonary disease, a combination of ipratropium and albuterol is more effective than either agent alone. An 85-day multicenter trial.," Chest 105:1411-1419 (1994).
Cydulka et al., "Effects of Combined Treatment with Glycopyrrolate and Albuterol in Acute Exacerbation of Chronic Obstructive Pulmonary Disease," Annals of Emergency Medicine, vol. 25, No. 4, pp. 470-473, Apr. 1995.
Cydulka et al., "Effects of Combined Treatment With Glycopyrrolate and Albuterol in Acute Exacerbation of Chronic Obstructive Pulmonary Disease," Annals of Emergency Medicine, vol. 25, No. 4, pp. 470-473 (1995).
Cydulka, R. et al., "Effects of Combined Treatment With Glycopyrrolate and Albuterol in Acute Exacerbation of Asthma," Annals Emergency Med. 23(2):270-274 (1994).
Dolovich, "Influence of Inspiratory Flow Rate, Particle Size, and Airway Caliber on Aerosolized Drug Delivery to the Lung," Respiratory Care, vol. 45, No. 6, Jun. 2000 (pp. 597-608).
Donohue, "Combination Therapy for Chronic Obstructive Pulmonary Disease Clinical Aspects," Proceedings of the American Thoracic Society, vol. 2, No Month 2005, (pp. 272-281).
Easton, P.A. et al., "A comparison of the bronchodilating effects of a beta-2 adrenergic agent (albuterol) and an anticholinergic agent (ipratropium bromide), given by aerosol alone or in sequence," New Engl. J. Med. 315:735-739 (1986) (Abstract).
European Search Report issued by the European Patent Office for Application No. 09739326.8 dated Jun. 5, 2013 (18 pages).
Faulds, D. et al., "Formoterol. A Review of its Pharmacological Properties and Therapeutic Potential in Reversible Obstructive Airways Disease," Drugs 42(1):115-137 (1991).
Food and Drug Administration, "Guidance for Industry: Chronic Obstructive Pulmonary Disease: Developing Drugs for Treatment," U.S. Department of Health and Human Services, Clinical/Medical, 17 pages (Nov. 2007).
Foradil Aerolizer package insert Jun. 2006.
Friedman, M. et al., "Pharmacoeconomic Evaluation of a Combination of Ipratropium Plus Albuterol Compared with Ipratropium Alone and Albuterol Alone in COPD," Chest 115:635-641 (1999).
Friedman, M., "Formoterol and ipratropium in COPD," Am. J. Resp. Cric. Care Med. 167:1579 (2003) (Abstract).
Gal, et al., "Glycopyrrolate and Atropine Inhalation: Comparative Effects on Normal Airway Function," AM REV RESPIR DIS, 1984, 129:871-873.
GB1008994.4 Examination Report dated Mar. 19, 2012.
Guidance for Industry, "Nasal Spray and Inhalation Solution, Suspension, and Spray Drug Products—Chemistry, Manufacturing and Controls Documentation," U.S. Department of Health and Human Services Food and Drug Administration Center for Drug Evaluation and Research (CDER) Jul. 2002 (49 pgs.).
Hansel et al., "Glycopyrrolate causes prolonged bronchoprotection and bronchodilation in patients with asthma," Chest 128:1974-1979 (2004).
Hekking, P.R. et al., "Long-term Efficacy of Formoterol Compared to Salbutamol," Lung (1990) Suppl:76-82.
Hess, "Medication Nebulizer Performance* Effects of Diluent Volume, Nebulizer Flow, and Nebulizer Brand," Chest, vol. 110, No. 2, Aug. 1996 (pp. 498-505).
Ida, H., "Cardiorespiratory Activities of 3-Formylamino-4-hydroxy-α-(N-1-methyl-2-p-methoxyphenethylaminomethyl)-benzylalcohol-hemifumarate (BD 40A) and some other β Adrenoceptor Stimulants in Conscious Guinea Pigs," Drug Res. 26(7): 1337-1340 (1976).
Jeppsson, A.B. et al., "On the Predictive Value of Experiments in vitro in the Evaluation of the Effect Duration of Bronchodilator Drugs for Local Administration," Pulmonary Pharmacology (1989) 2:81-285.

(56) References Cited

OTHER PUBLICATIONS

Johnson, B.E. et al., "Effect of inhaled glycopyrrolate and atropine in asthma. Precipitated by exercise and cold air inhalation," Chest 85:325-328 (1984).
Karpel, J.L., "Bronchodilator responses to anticholinergic and beta-adrenergic agents in acute and stable COPD," Chest 99:871-876 (1991) (Abstract).
Lee, T.A., et al., "Risk for Death Associated with Medications for Recently Diagnosed Chronic Obstructive Pulmonary Disease," Ann. Intern. Med. 149:380-390 (2008).
Lofdahl, C.G. et al., "Formoterol fumarate, a new β2-adrenoceptor agonist," Allergy 44:264-271 (1989).
Maesen, F.P. et al., "Bronchodilator effect of inhaled formoterol vs salbutamol over 12 hours," Chest 97:590-594 (1990).
Maesen, F.P. et al., "Formoterol in the treatment of nocturnal asthma," Chest 98:866-870 (1990).
Maesen, F.P. et al., "Formoterol suspension aerosol. Comparison with formoterol solution aerosol for 12 weeks in asthmatic patients," Chest 102:1544-1549 (1992).
Matera, M.G. et al., "A combination with clinical recommended dosages of salmeterol and ipratropium is not more effective than salmeterol alone in patients with chronic obstructive pulmonary disease," Resp. Med. 90:497-499 (1996).
Maynard et al., Pediatric Research, 1992, vol. 31 (4 part 2), p. 361.
Moore, R.H. et al., "Long-acting Inhaled L2-Agonists in Asthma Therapy," Chest 113:1095-1108 (1998).
Murase, K. et al., "Absolute Configurations of Four Isomers of 3-Formarnido-4-hydroxy-α-[[N-(p-methoxy-α-methylphenethyl)amino ]methyl]benzyl Alcohol, a Potent β-Adrenoceptor Stimulant," Chem. Pharm. Bull. 26(4):1123-1129 (1978).
Murase, K. et al., "New β-Adenoreceptor Stimulants. Studies on 3-Acylarnino-4-hydroxy-α-(N-substituted aminoethyl)benzyl Alcohols," Chem. Pharm. Bull.25( 6): 1368-13 77 ( 1977).
Naline, E. et al., "Relaxant effects and durations of action of formoterol and salmeterol on the isolated human bronchus," Eur. Respir. J. 7:914-920 (1994).
Newman, "Aerosol Deposition Considerations in Inhalation Therapy," Chest, vol. 88, No. 2, Aug. 1985 (pp. 152S-160S).
NZ 587561 Examination Report dated Jul. 11, 2012.
PCT/US09/35298 Search Report dated Sep. 29, 2009.
PCT/US2010/038045 International Preliminary Examination Report and Written Opinion dated Dec. 22, 2011.
Perforomist Prescribing Information Apr. 2007.
Puigbol, et al., "Nebulized Saline Solution of Dry Powder Formoterol is Useful for Acute Bronchospasm," AVFT 20(2): 128-130 (2001).
Pulmicort Respules package insert Aug. 4, 2000.
Pulmicort Respules package insert Jun. 2007.
Rebuck, A.S. et al., "Nebulized Anticholinergic and Sympathomimetic Treatment of Asthma and Chronic Obstructive Airways Disease in the Emergency Room," Am. J. Med. 82:59-64 (1987).
Rivera, "AirLife™ Brand Misty Max 10™ Nebulizer," Respiratory Care Products and Services, Dec. 18, 2002 (2 pgs.).
Ruffin, R.E. et al., "Combination bronchodilator therapy in asthma," J. Allergy Clin. Immunol. 69 (No. 1, Part 1):60-65 (1982).
Schroeckenstein et al., "Twelve-hour bronchodilation in asthma with a single dose of the anticholinergic compound glycopyrrolate" J. Allergy Clin. Immunol. 82(1):115-119 (1988).
Schuepp et al., "In Vitro Determination of the Optimal Particle Size for Nebulized Aerosol Delivery to Infants," J. Aerosol Medicine, 18(2):225-235 (2005).
Schultze-Werninghaus, G., "Multicenter 1-Year Trial on Formoterol, a New Long-Acting β2 Agonist, in Chronic Obstructive Airway Disease," Lung (1990) Suppl:83-89.

Seemann et al., "Improving Aerosol Drug Delivery in CF Therapy," 28th European Cystic Fibrosis Conference, Jun. 22-26, 2005 (1 pg.).
Seemann et al., "Improving Aerosol Drug Delivery in CR Therapy," 28th European Cystic Fibrosis Conference, Jun. 22-26, 2005 (1 pg.).
Shenfield, G.M., "Combination Bronchodilator Therapy," Drugs 24:414-439 (1982).
Shinkai, N. et al., "Tocolytic activity of formoterol against premature delivery in mice," JPP 54:1637-1643 (2002).
Shrestha, M. et al., "Decreased Duration of Emergency Department Treatment of Chronic Obstructive Pulmonary Disease Exacerbations With the Addition of Ipratropium Bromide to β-Agonist Therapy," Ann. Emerg. Med. 20:1206-1209 (1991).
Singh, S. et al., "Inhaled Anticholinergics and Risk of Major Adverse Cardiovascular Events in Patients with Chronic Obstructive Pulmonary Disease: A Systematic Review and Meta-analysis," JAMA 300(12):1439-1450 (2008).
Singh, S. et al., "NVA237, a once-daily inhaled antimuscarinic, provides 24-hour bronchodilator efficacy in patients with moderate-to-severe COPD," ATS International Conference Poster presented May 19-24, 2006.
Skorodin, Morton S. MD., "Pharmacotherapy for Asthma and Chronic Obstructive Pulmonary Disease," Archives of Internal Medicine, vol. 153, No. 7, pp. 814-828 (Apr. 1993) (Abstract).
Skorodin, "Pharmacotherapy for Asthma and Chronic Obstructive Pulmonary Disease," Arch. Intern. Med. 153(7):814-828 (1993).
Smaldone, "Assessing New Technologies: Patient-Device Interactions and Deposition," Respiratory Care, vol. 50, No. 9, Sep. 2005 (pp. 1151-1160).
Smith, C.M, et al., "The duration of action of the combination of fenoterol hydro bromide and ipratropium bromide in protecting against asthma provoked by hyper apnea," Chest 94:709-717 (1988).
Spiriva Handihaler package insert Aug. 31, 2006.
Sugiyama, H. et al., "The effect of formoterol on the late asthmatic phenomena in guinea pigs," J. Allergy Clin Immunol. 89:858-866 (1992).
Tashkin, Donald P., "The Role of Nebulizers in Airways Disease Management," US Respiratory Disease, Nebulization, pp. 27-31 (Jan. 1, 2007).
Ting, S. et al., "Nebulized Combined Formoterol and Budesonide (NCFB) for Children Younger than 5 Years of Age with Persistent Asthma," J. Allery Clin. Immunol. 111(1):8148 (2003) (Abstract).
Trofast, J. et al., "Steric aspects of Agonism and Antagonism at β-Adrenoceptors: Synthesis of and Pharmacological Experiments with the Enantiomers of Formoterol and Their Diastereomers," Chirality 3:443-450 (1991).
Tzelepis, G. et al., "Comparison of nebulized glycopyrrolate and metaproterenol in chronic obstructive pulmonary disease," Eur. Respir. J. 9:100-103 (1996).
Van Noord, J.A. et al., "Effects of Tiotropium with and without Formoterol on Airflow Obstruction and Resting Hyperinflation in Patients with COPD," Chest 129:509-517 (2006).
Walker et al., "Prolonged effect of inhaled glycopyrrolate in asthma," Chest 91(1):49-51 (1987).
Wallin, A. et al., "Formoterol, a new long acting beta 2 agonist for inhalation twice daily, compared with salbutamol in the treatment of asthma," Thorax 45:259-261 (1990).
Wesseling, G. et al., "A comparison of the effects of anticholinergic and beta-2-agonist and combination therapy on respiratory impedance in COPD," Chest 101: 166-173 (1992).
Wright, "Inhalation Dosage Forms," in Pharmaceutical Preformulation and Formulation A Practical Guide from Candidate Drug Selection to Commercial Dosage Form, ed. Gibson, No Month 2004, pp. 355-357 (11 total pages).
Ziment, I., "Unconventional therapy in asthma," Clin. Rev. Allergy Immunol. 14:289-320 ( 1996).

METHOD AND SYSTEM FOR THE TREATMENT OF CHRONIC COPD WITH NEBULIZED ANTICHOLINERGIC ADMINISTRATIONS

This application claims priority under 35 U.S.C. § 120 from U.S. nonprovisional patent application Ser. No. 15/050,280, filed Feb. 22, 2016, and claims priority under 35 U.S.C. § 120 from U.S. nonprovisional patent application Ser. No. 12/547,406, filed Aug. 25, 2009, and claims priority under 35 U.S.C. § 120 from U.S. nonprovisional patent application Ser. No. 12/393,709, filed Feb. 26, 2009, and claims priority under 35 U.S.C. § 119(e) from U.S. provisional patent application 61/031,639, filed Feb. 26, 2008, and from U.S. provisional patent application 61/080,184, filed Jul. 11, 2008, each of which applications is incorporated herein by reference in its entirety.

BACKGROUND OF THE INVENTION

Chronic obstructive airway disease (COPD) is a pulmonary (lung) disease characterized by chronic obstruction of the airways. COPD encompasses emphysema and chronic bronchitis. Chronic bronchitis is diagnosed where a patient suffers from chronic cough, mucus production, or both, for at least three months in at least two successive years where other causes of chronic cough have been excluded. In chronic bronchitis, airway obstruction is caused by chronic and excessive secretion of abnormal airway mucus, inflammation, and bronchospasm. Often chronic bronchitis is exacerbated by frequent or chronic infection.

Emphysema involves the destruction of elastin in terminal bronchioles, which leads to remodeling, destruction and ultimate collapse of the airway walls, Patients with emphysema gradually lose the ability to exhale, causing a rise in blood waste gasses (such as carbon dioxide), a drop in blood oxygen, and a general degradation of patient stamina and overall health. A characteristic of emphysema is permanent loss of alveoli. Remodeling leads to permanent enlargement of the air spaces distal to the terminal bronchioles, and destruction of terminal bronchiole walls, though without fibrosis. Emphysema is progressive with a poor prognosis. Since there is no known method for repairing elastin or restoring the alveoli, therapy is generally palliative and persistent.

Most patients suffering from COPD have both emphysema and chronic bronchitis. The standard of treatment for COPD includes maintenance and/or rescue dosing of bronchodilator and/or anti-inflammatory aerosol drugs. While most patients respond to treatment with metered dose inhalers or dry powder inhalers, there is a subset of patients for whom such options are not well-suited. Older and sicker COPD patients, for example, often find it difficult to use, or do not experience therapeutic benefit from the use of, metered dose inhalers or dry powder inhalers.

Dry powder inhalers are generally passive delivery devices, which patients actuate by forceful, controlled inhalation through the mouth. Metered dose inhalers, on the other hand, are in general active delivery devices, which create an atomized mist by forcing a drug solution or suspension through a nozzle under pressure. A patient activates the metered dose inhaler by pressing an actuator and simultaneously breathing in through the mouth in order to deposit the drug in the patient's lungs. Patients whose motor skills are impaired or not fully developed will often have trouble activating the device, coordinating their breathing, and generally using metered dose inhalers. Patients who also have poor inhalation capacity and control find dry powder inhalers to be difficult to operate as well. Newer inhaler devices that are breath-actuated or produce a soft mist are easier for patients to operate; but these newer devices still require coordination and a breath-hold; and achievement of sufficient lung deposition and distribution is reliant on only one or two inhalations. For sicker and older COPD patients, nebulizer delivery of their medicines is an important delivery option, since they can generally receive a full dose regardless of disease state, because all that is required is normal (tidal) breathing over multiple minutes.

There are two general categories of bronchodilators muscarinic antagonists and beta 2-adrenergic agonists, Muscarinic antagonists are preferred and are recommended first-line therapy for maintenance treatment of moderate to severe COPD. Long-acting muscarinic antagonists (so-called LAMAS) are preferred to short-acting muscarinic antagonists, due to their superior efficacy and duration of effect. One LAMA that has been approved for use in cam in the United States is tiotropium bromide powder for inhalation (Spirivat, NDA No, 021395, Boehringer Ingelheim), Tiotropium bromide is available commercially only as a dry powder, which is administered by a breath-activated inhaler. A similar mode of administration is disclosed by Bannister et al. (U.S. Pat. No. 7,229,607) for administration of glycopyrronium bromide (glycopyrrolate) as a dry powder. The '607 patent claims a method for achieving grater than 20 hours of bronchodilation in a COPD patient by means of coated particles in a dry powder formulation. The '607 patent distinguishes this methodology from administration of a solution formulation of glycopyrrolate, which is characterized as being unable to achieve effective treatment of COPD for longer than 12 hours. For example, Bannister et al. state: "Schroeckenstein et al., J. Allergy Clin. Immunol., 1988; 82(1): 115-119, discloses the use of glycopyrrolate in an aerosol formulation for treating asthma. A single administration of the metered-dose glycopyrrolate aerosol achieved bronchodilation over a 12 hour period." Additionally, Bannister et al. admit: "Skorodin, Arch Intern, Med, 1993; 153: 814 828, discloses the use of glycopyrrolate in an aerosol formulation for the treatment of asthma and COPD. It is stated that, in general, the quaternary ammonium anticholinergic compounds have a duration of action of 4 to 12 hours. A dose of between 0.2 to 1.0 mg of glycopyrrolate is recommended at 6 to 12 hour intervals." And the inventors of the '607 patent also state: "Walker et al., Chest, 1987; 91(1): 49-51, also discloses the effect of inhaled glycopyrrolate as an asthma treatment. Again, the duration of effective treatment is shown to be up to 12 hours, although up to 8 hours appears to be maximal."

Hansel et al. ("Glycopyrrolate causes prolonged bronchoprotection and bronchodilation in patients with asthma," 128 Chest 1974-1979 (2005)) claim to have demonstrated an improvement in bronchodilation and bronchoprotection in mild-to-moderate asthmatic patients for a period of up to 30 h with nebulized glycopyrronium bromide (glycopyrrolate). Single doses of glycopyrrolate (0.5, 1.0 and 2.0 mg/dose) were administered to mild-to-moderate asthmatic volunteers ages 18-60, who were then challenged with doubling increments of methacholine dose until a >20% fall in $FEV_1$ was achieved. A log dose-response curve was constructed with these data by linear interpolation. No clear dose-response was observed for either bronchodilation or bronchoprotection. Although the authors claim to have demonstrated bronchodilation for a period of up to 30 h, the mean response in $FEV_1$ was clinically meaningful (>10% change from pre-dose levels) only at 2 hours post-dose and dropping to approximately 5% levels from 12 h through 30 h. This indicates that the bronchodilator response was short-lived and not sustainable beyond 12 hours. In the same study, the authors demonstrated clinically meaningful bronchoprotective effect of nebulized glycopyrrolate that was sustained up to 30 h at all dose levels. Although the bronchoprotective effect in response to a bronchial challenge test is considered a useful surrogate test for treatment of lung diseases with airway hyperresponsiveness, such as asthma, a positive bronchoprotective test is not considered a predictive tool and useful test in patients with COPD, because of the different disease pathology and mechanisms involved in COPD. As outlined in the literature and international guidelines, the airway hyperresponsiveness test is not considered a suitable test for use in COPD, therefore the data in asthma patients presented by Hansel et al. cannot be extrapolated for COPD. In any case, the authors seem to favor a breath-activated dry powder inhaler as the optimal mode of delivery. Id. at 1978. Thus, this study can be seen as being supportive of the dry powder inhalation methodology taught by Bannister et al. (U.S. Pat. No. 7,229,607). Hansel et al. list as conclusions that nebulized glycopyrrolate may have a sustained duration of action and be superior to ipratropium bromide for treatment of stable COPD. Id. at 1974. Nevertheless none of the treated patients in Hansel, et al were identified as suffering from COPD, and no study has demonstrated a clinically meaningful bronchodilator response in COPD, asthma, or any other respiratory disease with nebulized glycopyrrolate for greater than 12 hours at any dose.

A sub-segment of the COPD population comprising the sickest and oldest patients requires nebulizer delivery of their medicines because they are unable to satisfactorily operate a metered dose or dry powder inhaler. However, the treatment options for these patients are limited. Although two long-acting beta 2 agonist solution formulations are approved for nebulizer delivery twice daily (BID), and indicated for the maintenance treatment of COPD symptoms, muscarinic antagonists are preferable for the treatment of moderate to severe COPD. Also, once-daily dosing (QD) is preferable to BID. Ipratropium bromide is the only muscarinic antagonist approved for nebulizer delivery in COPD (monotherapy or in combination with albuterol), however ipratropium +/− albuterol is indicated for administration four times per day (QID); and QID dosing and long nebulization times of this short-acting agent is inconvenient, leading to poor compliance and thus sub-optimal clinical outcomes. Longer acting aerosol drugs have been demonstrated to generally be more efficacious and result in better compliance compared to shorter acting drugs.

There is thus a need for additional therapeutic options for the treatment of COPD. There is a need for therapeutic options that offer greater convenience and better efficacy, especially for the sub-population of COPD patients who require nebulizer delivery. In particular there is a need for a nebulized muscarinic antagonist that provides more than 12 hours, and preferably at least 24 hours of therapeutic benefit to COPD patients. Heretofore, no method, device or system has been suggested that satisfies these needs.

SUMMARY OF THE INVENTION

The foregoing and further needs are satisfied by embodiments of the present invention. Some embodiments provide long-acting treatment of one or more symptoms of COPD. Embodiments described herein provide methods, devices and systems that permit relief of one or more symptoms of COPD for a period of at least about 18 hr, preferably at least about 20 hours, and more preferably at least about 24 hours, with nebulized administration of an antimuscarinic agent, such as glycopyrronium bromide (glycopyrrolate). In particular embodiments set forth herein, there are provided methods, devices and systems for administration of an antimuscarinic agent, such as glycopyrrolate, via a high efficiency nebulizer. High efficiency nebulizers provide shorter treatment times and superior lung deposition as compared to conventional nebulizers. High efficiency nebulizers can produce smaller particle sizes with tighter particle size distributions, which can result in more drug depositing in the lungs, and less drug depositing in the oropharyngeal pathway. This is particularly advantageous for delivering a muscarinic antagonist that has as a close-limiting side effect dry mouth, which can limit the amount of drug that can be delivered to, and tolerated by, the patient, and thereby prevent achievement of maximal duration of therapeutic benefit. Also, smaller particles tend to penetrate more homogenously and farther into the lungs, thereby enhancing distribution of the drug throughout the surface of the lungs and targeting a greater proportion of muscarinic receptors that are involved in the pathogenesis of one or more symptoms of cam Without wishing to be bound by theory, the inventors believe that the enhanced deposition, distribution or both of a long-acting muscarinic antagonist with a high efficiency nebulizer (as opposed to a conventional nebulizer) enhances outcomes in the treatment of COPD. In an exemplary embodiment, a nebulizer capable of delivering droplets having a median particle diameter of less than about 4.5 μm (especially less than about 4.0 μm) and a geometric standard deviation (GSD) of less than about 2.0, (especially less than about 1.8) will provide more efficacious and better-tolerated treatment of COPD with an antimuscarinic agent as compared to a conventional nebulizer. Some embodiments provide a unit dosage form adapted or adaptable for administering a nominal dose of a muscarinic antagonist, such as glycopyrrolate, with a high efficiency nebulizer for treatment of COPD. Some embodiments provide a device comprising (1) a combination of a unit dosage form adapted or adaptable for administering a nominal dose of a muscarinic antagonist, such as glycopyrrolate, with a high efficiency nebulizer for treatment of COPD; and (2) a high efficiency nebulizer.

Furthermore, previous published reports of delivery of a glycopyrrolate solution formulation by nebulizer were at concentrations of no more than 0.2 mg/ml and contained a preservative, benzyl alcohol, that is a known lung irritant. Without wishing to be bound by theory, it is believed that a higher concentration of glycopyrrolate at the muscarinic receptor level and a more selective targeting of the muscarinic receptors (higher quantity of receptor binding) in the airways will contribute to a faster onset and/or greater magnitude of therapeutic effect and/or a greater duration of therapeutic effect. Additionally, eliminating the preservative enables higher or more concentrated doses of glycopyrrolate to be delivered in a better-tolerated manner.

Some embodiments described herein provide a method of treating a patient having chronic obstructive pulmonary disease (COPD), comprising administering to the patient, with a high efficiency nebulizer, a nominal dose of a composition comprising a muscarinic antagonist that provides the patient with a therapeutic effect for at least about 24 hours. Also provided are systems for carrying out the aforementioned method, comprising a formulation to be nebulized and a high efficiency nebulizer. Some embodiments described herein provide a method of treating a patient having chronic obstructive pulmonary disease (COPD), comprising administering to the patient, with a high efficiency nebulizer, a nominal dose of a composition comprising a muscarinic antagonist, wherein administering said nominal dose with said high efficiency nebulizer provides to the patient: (1) an increased magnitude and/or duration of therapeutic effect; and (2) reduced or acceptable side effects, compared to administering the same nominal dose of the muscarinic antagonist with a conventional nebulizer. Some embodiments comprise administering said nominal dose with the high efficiency nebulizer to the patient that results in therapeutically acceptable side effects. In some embodiments, the method comprises administering said nominal dose of the composition with the high efficiency nebulizer to the patient that results in reduced side effects compared to administering the same nominal dose with a conventional nebulizer. In some embodiments, the method comprises administering said nominal dose of the composition with the high efficiency nebulizer produces a calculated respirable dose of the muscarinic antagonist, whereby the patient experiences reduced side effects compared to administering a nominal dose that is calculated to achieve the same respirable dose with a conventional nebulizer. In some embodiments, the method comprises administering said nominal dose of the composition with the high efficiency nebulizer achieves a deposited lung dose of the muscarinic antagonist, whereby the patient experiences reduced side effects compared to administering a nominal dose that achieves substantially the same deposited lung dose with a conventional nebulizer. In some embodiments, the composition comprising the muscarinic antagonist is a concentrated, preservative-free, pH-adjusted solution formulation of the muscarinic antagonist. In some embodiments, e.g. when the muscarinic antagonist is glycopyrrolate, the concentration of the muscarinic antagonist is about 25 to about 400 µg/mL. In some embodiments, the composition has a pH of 3 to 5. In some embodiments, the formulation is room temperature stable for at least 2 years. In some embodiments, the composition comprising the muscarinic antagonist contains about 50 µg to about 1000 µg of glycopyrrolate as the muscarinic antagonist. In some embodiments, the composition has a volume of about 1.0 mL or less, e.g. 0.1 to 1.0 mL (especially 0.3 to 0.7 mL) or 0.5 mL. In some embodiments, the composition is administered in about 3 minutes or less. In some embodiments, the solution has a stabilizing excipient. In some embodiments, the stabilizing excipient is ethylenediaminetetraacetic acid (EDTA) or a pharmaceutically acceptable salt thereof. In some embodiments, the composition further comprises an excipient to mitigate side effects, for example dry mouth. In some embodiments, the excipient comprises citric acid or a pharmaceutically acceptable salt thereof. In some embodiments, the muscarinic antagonist is a long-acting muscarinic antagonist. In some embodiments, the nominal dose of the composition comprising the muscarinic antagonist contains about 25 µg to about 2000 µg, about 25 µg to about 1000 µg, or about 50 µg to about 1000 µg of glycopyrrolate as the muscarinic antagonist. In some embodiments, the nominal dose of the composition comprising the muscarinic antagonist contains about 25 µg to about 2000 µg, about 25 µg to about 1000 µg, about 25 µg to about 500 µg, about 25 µg to about 350 µg, about 25 µg to about 300 µg, about 25 µg to about 250 µg, about 25 µg to about 200 µg, about 50 µg to about 2000 µg, about 50 µg to about 1000 µg, about 50 µg to about 500 µg, about 50 µg to about 350 µg, about 50 µg to about 300 µg, about 50 µg to about 250 µg, about 50 µg to about 200 µg, about 75 µg to about 2000 µg, about 75 µg to about 1000 µg, about 75 µg to about 500 µg, about 75 µg to about 350 µg, about 75 µg to about 300 µg, about 75 µg to about 250 µg, about 75 µg to about 200 µg, about 100 µg to about 2000 µg, about 100 µg to about 1000 µg, about 100 µg to about 500 µg, about 100 µg to about 350 µg, about 100 µg to about 300 µg, about 100 µg to about 250 µg, about 100 µg to about 200 µg, about 50 µg, about 75 µg, about 100 µg, about 125 µg, about 150 µg, about 175 µg, about 200 µg, about 225 µg, about 250 µg, about 275 µg, 300 µg, about 325 µg, about 350 µg, about 400 µg, about 450 µg, about 475 µg, about 500 µg, about 525 µg, about 550 µg, about 575 µg, about 600 µg, about 625 µg, about 650 µg, about 675 µg, about 700 µg, about 725 µg, about 750 µg, about 775 µg, about 800 µg, about 825 µg, about 850 µg, about 875 µg, about 900 µg, about 925 µg, about 950 µg, about 975 µg, about 1000 µg, about 1250 µg, about 1500 µg, about 1750 µg, about 2000 µg of glycopyrrolate as the muscarinic antagonist. In some embodiments, the high efficiency nebulizer emits droplets having a Mass Median Aerodynamic Diameter (MMAD) of less than about 4.5 µm and a geometric standard deviation (GSD) of less than about 2.0, or optimally an MMAD of less than 4.0 µm and a GSD less than 1.8. In some embodiments, the therapeutic effect comprises an improvement of $FEV_1$ above baseline of at least about 10% at 24 hours after the composition is administered with the high efficiency nebulizer. In some embodiments, the therapeutic effect comprises an improvement of FI above baseline of at least about 100 at 24 hours after the composition is administered with the high efficiency nebulizer. In some embodiments, the composition further comprises a beta 2-adrenoceptor agonist, a corticosteroid, or both.

Some embodiments described herein provide an inhalation system for the treatment or prophylaxis of a respiratory condition in a patient, the system comprising: (a) a nominal dose of a muscarinic antagonist in an aqueous inhalation solution; and (b) a high efficiency nebulizer, wherein administration of the muscarinic antagonist with the inhalation device provides muscarinic antagonist lung deposition (deposited or calculated lung dose) of at least about 30%, at least about 35%, at least about 40%, at least about 45%, at least about 50%, at least about 55%, at least about 60%, about 30% to about 60%, about 30% to about 55%, about 30% to about 50%, about 30% to about 40%, about 30% to about 75%, about 40% to about 70%, or about 45% to about 60%, of the nominal dose of the muscarinic antagonist. Some embodiments provide a unit dosage form, which comprises a container that holds a nominal dose of a composition comprising a muscarinic antagonist, such as glycopyrrolate, said container being adapted or adaptable to operate with a high efficiency nebulizer to carry out the foregoing method. Some embodiments provide a combination of (1) a high efficiency nebulizer and (2) the aforementioned unit dosage form.

Some embodiments described herein provide a composition for administration with a high efficiency nebulizer, comprising a concentrated, preservative-free, pH-adjusted solution formulation of the muscarinic antagonist. In some embodiments, the muscarinic antagonist is glycopyrrolate. In some embodiments, the glycopyrrolate formulation has a concentration of about 50 to about 400 µg/mL. In some embodiments, the glycopyrrolate formulation has a concentration of at least 0.5 mg/mL. In some embodiments, the glycopyrrolate has a concentration of at least 1 mg/mL. In some embodiments, the pH is about 3 to about 5, and the composition contains a beta 2-adrenoceptor agonist (e.g. albuterol, levalbuterol, salmeterol, formoterol, or arformoterol), and/or a corticosteroid (budesonide, fluticasone, ciclesonide). In some embodiments, the composition further comprises a non-steroidal anti-inflammatory agent. In some embodiments, the composition is administered with a high efficiency nebulizer in 2 minutes or less.

Some embodiments described herein provide a method of treating a patient having chronic obstructive pulmonary disease (COPD), comprising administering to the patient, with a high efficiency nebulizer, a composition comprising a muscarinic antagonist that provides to the patient a respirable dose or deposited dose of a muscarinic antagonist, wherein achievement of said respirable dose or deposited dose with said high efficiency nebulizer provides to the patient: (1) a similar or an increased magnitude and/or duration of therapeutic effect; and (2) reduced or acceptable side effects, compared to achievement of the same respirable dose or deposited dose of the muscarinic antagonist with a conventional nebulizer. In some embodiments, achievement of the respirable dose or deposited dose with the high efficiency nebulizer produces in the patient an increased duration of therapeutic effect of at least 24 hours after administration of the nominal dose. In some embodiments, the therapeutic effect comprises an improvement of $FEV_1$ of at least about 100 mL above baseline when adjusted for placebo or at least about 10% above baseline, when adjusted for placebo, 24 hours after the composition is administered with the high efficiency nebulizer.

Some embodiments described herein provide a method of treating a patient having chronic obstructive pulmonary disease (COPD), comprising administering to the patient, with a nebulizer, a dose of glycopyrrolate, wherein the administration produces in the patient an area under the plasma concentration curve of glycopyrrolate (AUC) of at least about 100 pg/mL·hr. In some embodiments, the administration of the dose of glycopyrrolate achieves in the patient a ratio of AUC to maximum plasma concentration of glycopyrrolate (Cmax) of at least about 0.6 hr, at least about 0.75 hr, at least about 1.0 hr, at least about 1.25 hr, or at least about 1.5 hr. in some embodiments, the method results in a therapeutic effect for at least about 24 hours after administering the glycopyrrolate. In some embodiments, the glycopyrrolate dose is about 25 µg to about 1000 µg of glycopyrrolate. In some embodiments, the glycopyrrolate dose is about 25 µg to about 400 µg of glycopyrrolate. In some embodiments, the therapeutic effect comprises an improvement of $FEV_1$ of at least about 100 mL above baseline when adjusted for placebo or at least about 10% above baseline when adjusted for placebo 24 hours after the glycopyrrolate is administered with the nebulizer. In some embodiments, the nebulizer is a high efficiency nebulizer.

Some embodiments described herein provide an inhalation system for the treatment or prophylaxis of a respiratory condition in a patient, the system comprising: (a) a nominal dose of a muscarinic antagonist in an aqueous inhalation solution; and (b) an inhalation device, wherein the aqueous inhalation solution provides a duration of therapeutic effect of at least about 12 hr, about 12 hr to about 24 hr, about 18 hr to about 24 hr, about 20 hr to about 24 hr or at least about 24 hr.

BRIEF DESCRIPTION OF THE DRAWINGS

Examples of aspects of the current invention are illustrated in the attached figures, of which.

DETAILED DESCRIPTION OF THE INVENTION

Figure 1:
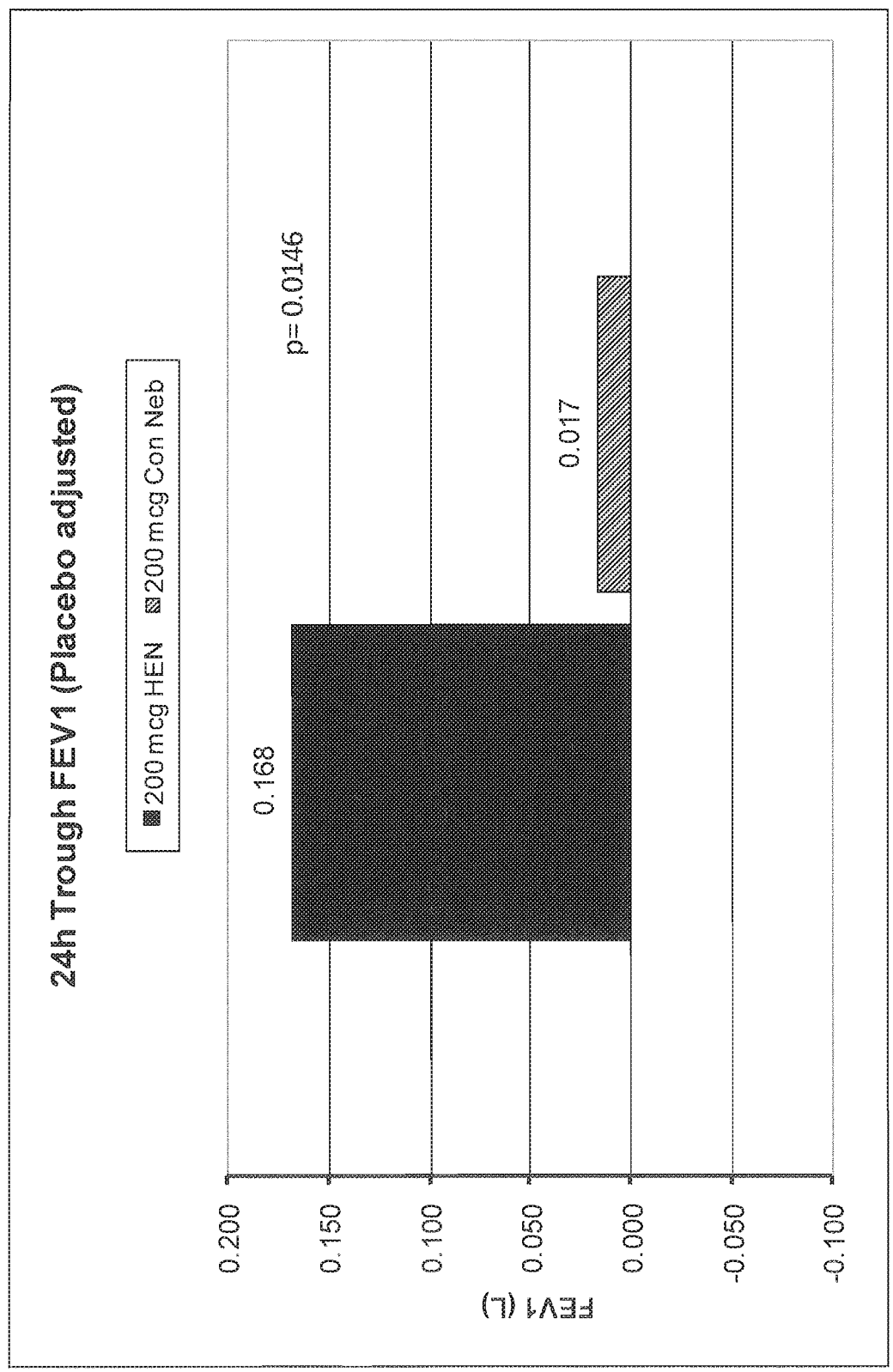
FIG. 1 is a graph comparing the placebo-adjusted 24-hour (trough) $FEV_1$ (L) obtained by administering a 200 µg dose of glycopyrrolate with a high efficiency nebulizer (PARI eFlow®) and a conventional jet nebulizer.

Unless defined otherwise, all technical and scientific terms used herein have the same meaning as commonly understood by one of skill in the art to which the inventions described herein belong. All publications, patents, and patent applications mentioned in this specification are herein incorporated by reference to the same extent as if each individual publication, patent, or patent application was specifically and individually indicated to be incorporated by reference.

Definition of Terms

As used herein, the term "about" is used synonymously with the term "approximately." Illustratively, the use of the term "about" with regard to a certain therapeutically effective pharmaceutical dose indicates that values slightly outside the cited values, e.g. plus or minus 0.1% to 10%, which are also effective and safe.

As used herein, the terms "comprising," "including," "such as," and "for example" (or "e.g.")) are used in their open, non-limiting sense.

As used herein "mcg" means micrograms, and is synonymous with "µg" "µg". One microgram is 0.001 mg, or 0.000001 g.

As used herein, the phrase "consisting essentially of" is a transitional phrase used in a claim to indicate that the following list of ingredients, parts or process steps must be present in the claimed composition, machine or process, but that the claim is open to unlisted ingredients, parts or process steps that do not materially affect the basic and novel properties of the invention.

"Nominal dose," as used herein, refers to the loaded dose, which is the amount of active pharmaceutical ingredient ("API") in an inhalation device prior to administration to the patient. The volume of solution containing the nominal dose is referred to as the "fill volume."

"$AUC_{(0-1)}^{HEN}$" as used herein, refers to the area under a blood plasma concentration curve up to the last time point for the nominal dose of active pharmaceutical ingredient (API) administered with a high efficiency nebulizer.

"$AUC_{(0-1)}^{Conv}$" as used herein, refers to the area under a blood plasma concentration curve up to the last time point for a nominal dose of active pharmaceutical ingredient (API) administered with a conventional nebulizer.

"$AUC_{(0-\infty)}^{HEN}$" as used herein, refers to the area under a blood plasma concentration curve for a nominal dose of active pharmaceutical ingredient (API) administered with a high efficiency nebulizer.

"$AUC_{(0-\infty)}^{Conv}$" as used herein, refers to the area under a blood plasma concentration curve for a nominal dose of active pharmaceutical ingredient (API) administered with a conventional nebulizer [$AUC_{(0-\infty)}^{Conv}$].

"Substantially the same nominal dose" as used herein, means that a first nominal dose of an active pharmaceutical ingredient (API) contains approximately the same number of millimoles of the muscarinic antagonist as a second nominal dose of the muscarinic antagonist.

"Bioavailability" as used herein, refers to the amount of unchanged drug that reaches the systemic circulation. By definition, the bioavailability of an intravenous solution containing the active pharmaceutical ingredient (API) is 100%.

"Enhanced lung deposition," as used herein, refers to an increase in drug deposition (deposited lung dose) arising out of, for example, the improved efficiency of drug delivery with a high efficiency nebulizer. In general, a high efficiency nebulizer will produce a drug cloud having a greater respirable fraction than a conventional nebulizer. While not wishing to be bound by theory, it is considered that a greater respirable fraction will permit greater lung deposition and concomitantly lower oropharyngeal deposition of the drug. In some embodiments, it is considered that reduced oropharyngeal deposition of drug will reduce local side effects, for example dry mouth.

"Deposited dose" or "deposited lung dose" is the amount of muscarinic antagonist deposited in the lung. The deposited dose or deposited lung dose may be expressed in absolute terms, for example the number of µg of API deposited in the lungs. The deposited lung dose may be expressed as a percentage of the nominal dose deposited in the lungs. The deposited lung dose may also be expressed in relative terms, for example comparing the mass of API deposited in the lungs with a high efficiency nebulizer to the mass of API deposited in the lungs with a conventional nebulizer.

"$C_{max}^{HEN}$" as used herein, refers to the maximum blood plasma concentration for a nominal dose of the active pharmaceutical ingredient (API) administered with a high efficiency nebulizer.

"$C_{max}^{Conv}$" as used herein, refers to the maximum blood plasma concentration for a nominal dose of the active pharmaceutical ingredient (API) administered with a conventional nebulizer.

"Enhanced pharmacokinetic profile" means an improvement in some pharmacokinetic parameter. Pharmacokinetic parameters that may be improved include, $AUC_{last}$, $AUC_{(0-\infty)}$ $T_{max}$, and optionally a $C_{max}$. In some embodiments, the enhanced pharmacokinetic profile may be measured quantitatively by comparing a pharmacokinetic parameter obtained for a nominal dose of an active pharmaceutical ingredient (API) administered with one type of inhalation device (e.g. a high efficiency nebulizer) with the same pharmacokinetic parameter obtained with the same nominal dose of active pharmaceutical ingredient (API) administered with a different type of inhalation device.

"Blood plasma concentration" refers to the concentration of an active pharmaceutical ingredient (API) in the plasma component of blood of a subject or patient population.

"Respiratory condition," as used herein, refers to a disease or condition that is physically manifested in the respiratory tract, including, but not limited to, chronic obstructive pulmonary disease (COPD)), bronchitis, chronic bronchitis, emphysema, asthma, or reactive airway disorder (RAD).

"Patient" refers to the animal (especially mammal) or human being treated.

"Muscarinic antagonist" refers to antimuscarinic agents, which are compounds that have the ability to inhibit the action of the neurotransmitter acetylcholine by blocking its binding to muscarinic cholinergic receptors. These agents can be long-acting or short-acting. Long-acting muscarinic antagonists have a therapeutic effect lasting greater than about 6 hours. Some long-acting muscarinic antagonists include, but are not limited to, glycopyrrolate, tiotropium, aclidinium, trospium, darotropium, QAT 370, GSK 233705, GSK 573719, GSK 656398, TD4208, BEA 218 or a pharmaceutical acceptable derivative, salt, enantiomer, diastereomer, or racemic mixture thereof. Short-acting muscarinic antagonists have a therapeutic effect for less than about 6 hours. Some short-acting muscarinic antagonists include, but are not limited to, ipratropium, oxitropium, or a pharmaceutical acceptable derivative, salt, enantiomer, diastereomer, or racemic mixture thereof. In some embodiments, the "muscarinic antagonist" is glycopyrrolate, tiotropium, aclidinium, trospium, QAT370, GSK233705, GSK 656398, BEA2180, ipratropium, oxitropium, oxybutynin or a pharmaceutical acceptable derivative, salt, enantiomer, diastereomer, or a pharmaceutical acceptable derivative, salt, enantiomer, diastereomer, or racemic mixture thereof.

"Nebulizer," as used herein, refers to a device that turns medications, compositions, formulations, suspensions, and mixtures, etc. into a fine mist for delivery to the lungs. Nebulizers may also be referred to as atomizers.

"Drug absorption" or simply "absorption" typically refers to the process of movement of drug from site of delivery of a drug across a barrier into a blood vessel or the site of action, e.g., a drug being absorbed in the pulmonary capillary beds of the alveoli.

[$T_{max}^{HEN}$] as used herein, refers to the amount of time necessary for a nominal dose of an active pharmaceutical ingredient (API) to attain maximum blood plasma concentration after administration with a high efficiency nebulizer.

[T1/2] Half-life: T1/2 in reference to the elimination rate of a drug, such as a muscarinic antagonist (e.g. glycopyrrolate) is the amount of time necessary for the drug's plasma concentration to drop to one-half of its initial plasma concentration.

[$T_{max}^{Conv}$] as used herein, refers to the amount of time necessary for a nominal dose of an active pharmaceutical ingredient (API) to attain maximum blood plasma concentration after administration with a conventional nebulizer.

The term "treat" and its grammatical variants (e.g. "to treat," "treating," and "treatment") refer to administration of an active pharmaceutical ingredient to a patient with the purpose of ameliorating or reducing the incidence of one or more symptoms of a condition or disease state in the patient. Such symptoms may be chronic or acute; and such amelioration may be partial or complete. In the present context, treatment entails administering a muscarinic antagonist (optionally in combination with a beta 2-adrenoceptor agonist) to a patient via a pulmonary inhalation route.

The term "prophylaxis" refers to administration of an active pharmaceutical ingredient to a patient with the purpose of reducing the occurrence or recurrence of one or more acute symptoms associated with a disease state in the patient. In the present context, prophylaxis entails administering a muscarinic antagonist (optionally in combination with a beta 2-adrenoceptor agonist) to a patient via a pulmonary inhalation route. Thus, prophylaxis includes reduction in the occurrence or recurrence rate of acute exacerbations in chronic obstructive pulmonary disease (COPD). However, prophylaxis is not intended to include complete prevention of onset of a disease state in a patient who has not previously been identified as suffering from a pulmonary condition or disease; nor does prophylaxis include prevention of pulmonary cancer.

As used herein, a difference is "significant" if a person skilled in the art would recognize that the difference is probably real. In some embodiments, significance may be determined statistically in which case two measured parameters may be referred to as statistically significant. In some embodiments, statistical significance may be quantified in terms of a stated confidence interval (CI), e.g. greater than 90%, greater than 95%, greater than 98%, etc. In some embodiments, statistical significance may be quantified in terms of a p value, e.g. less than 0.5, less than 0.1, less than 0.05, etc. The person skilled in the art will recognize these expressions of significance and will know how to apply them appropriately to the specific parameters that are being compared.

In some embodiments described herein an active pharmaceutical ingredient (API) is a muscarinic antagonist. In some embodiments, the API is substantially free of other bronchodilating agents, such as beta 2-adrenoceptor agonists, like formoterol, salmeterol and salbutamol (albuterol). In this context, "substantially free of other bronchodilating agents" indicates that the solution contains no other bronchodilating agent or contains less than a quantity of another bronchodilating agent that would be sufficient to materially affect the properties of the muscarinic antagonist solution. In some embodiments, the API is a muscarinic antagonist (optionally in combination with a beta 2-adrenoceptor agonist and/or in combination with an anti-inflammatory agent which could include a corticosteroid or a non-steroidal anti-inflammatory drug (NSAID)). In some embodiments, the API is free of other bronchodilating agents, such as beta 2-adrenoceptor agonists, like formoterol, salmeterol and salbutamol (albuterol). In this context, "free of other bronchodilating agents" means that the solution contains no other bronchodilating agent than the recited muscarinic antagonist, or contains less than a detectable amount of the other bronchodilating agents.

Methods and Systems for the Treatment of Respiratory Conditions with HENs

The present invention provides methods and inhalation systems for treatment or prophylaxis of a respiratory condition in a patient, such as chronic obstructive pulmonary disease (COPD), and optionally chronic bronchitis and/or emphysema. In some embodiments, the methods and inhalation systems comprise administering to a patient a nominal dose of an active pharmaceutical ingredient (API), muscarinic antagonist (optionally in combination with a beta 2-adrenoceptor agonist and/or in combination with an anti-inflammatory agent which could include a corticosteroid or a non-steroidal anti-inflammatory drug (NSAID)) in an aqueous inhalation solution with a high efficiency nebulizer (HEN), wherein delivering the nominal dose of the muscarinic antagonist to the patient provides one or more of the following advantages: (1) an enhanced pharmacokinetic profile as compared to administration with a conventional nebulizer; (2) an enhanced therapeutic effect as compared to administration with a conventional nebulizer; (4) an enhanced lung deposition (deposited lung dose) evidenced by scintigraphy or deconvolution, or derived from suitable in vitro indicators such as RDDR, RF, GSD, and/or a MMAD values as compared to administration with a conventional nebulizer; (5) reduced administration times, periods, and/or volumes as compared to administration with a conventional nebulizer; (6) a reduction in adverse side effects associated with API treatment and optionally a longer duration of therapeutic effect as compared to administration with a conventional nebulizer; (7) optional administration with a beta 2-adrenoceptor agonist and optionally a corticosteroid; and (8) an enhanced method of treatment of acute exacerbations of a respiratory condition in a patient, e.g. COPD. In some embodiments, the methods and inhalation systems comprise administering to a patient a nominal dose of an increased concentration of API in an aqueous inhalation device, metered dose inhaler (MD"), conventional nebulizer, or high efficiency nebulizer.

Inhalation Therapy

An inhalation device, as used herein, refers to any device that is capable of administering a solution to the respiratory airways of a patient. Inhalation devices include conventional inhalation devices, such as metered dose inhalers (MDIs), conventional nebulizers, such as jet nebulizers, and high efficiency nebulizers, such as vibrating membrane nebulizers.

Inhalation nebulizers, or atomizers, are also commonly used for the treatment of respiratory diseases. Inhalation nebulizers deliver therapeutically effective amounts of pharmaceuticals by forming an aerosol which includes droplet sizes that can easily be inhaled. The aerosol can be used, for example, by a patient within the bounds of an inhalation therapy, whereby the therapeutically effective pharmaceutical or drug reaches the patient's respiratory tract upon inhalation.

High Efficiency Nebulizers

High efficiency nebulizers are inhalation devices that comprise a microperforated membrane through which a liquid solution is converted through electrical or mechanical means into aerosol droplets suitable for inhalation. High efficiency nebulizers can deliver a large fraction of a loaded dose to a patient. In some embodiments, the high efficiency nebulizer also utilizes one or more actively or passively vibrating microperforated membranes. In some embodiments, the high efficiency nebulizer contains one or more oscillating membranes. In some embodiments, the high efficiency nebulizer contains a vibrating mesh or plate with multiple apertures and optionally a vibration generator with an aerosol mixing chamber. In some such embodiments, the mixing chamber functions to collect (or stage) the aerosol from the aerosol generator. In some embodiments, an inhalation valve is also used to allow an inflow of ambient air into the mixing chamber during an inhalation phase and is closed to prevent escape of the aerosol from the mixing chamber during an exhalation phase. In some such embodiments, the exhalation valve is arranged at a mouthpiece which is removably mounted at the mixing chamber and through Which the patient inhales the aerosol from the mixing chamber. Still yet, in some embodiments, the high efficiency nebulizer contains a pulsating membrane. In some embodiments, the high efficiency nebulizer is continuously operating.

In some embodiments, the high efficiency nebulizer contains a vibrating microperforated membrane of tapered nozzles that generates a plume of droplets without the need for compressed air. In these embodiments, a solution in the microperforated membrane nebulizer is in contact with a membrane, the opposite side of which is open to the air. The membrane is perforated by a large number of nozzle orifices of an atomizing head. An aerosol is created when alternating acoustic pressure in the solution is built up in the vicinity of the membrane causing the fluid on the liquid side of the membrane to be emitted through the nozzles as uniformly sized droplets.

Some embodiments of high efficiency nebulizers use passive nozzle membranes and a separate piezoelectric transducer that stimulates the membrane. In contrast, some high efficiency nebulizers employ an active nozzle membrane, which use the acoustic pressure in the nebulizer to generate very fine droplets of solution via the high frequency vibration of the nozzle membrane.

Some high efficiency nebulizers contain a resonant system. In some such high efficiency nebulizers, the membrane is driven by a frequency for which the amplitude of the vibrational movement at the center of the membrane is particularly large, resulting in a focused acoustic pressure in the vicinity of the nozzle; the resonant frequency may be about 100 kHz. A flexible mounting is used to keep unwanted loss of vibrational energy to the mechanical surroundings of the atomizing head to a minimum. In some embodiments, the vibrating membrane of the high efficiency nebulizer may be made of a nickel-palladium alloy by electroforming.

In some embodiments, the high efficiency nebulizer achieves lung deposition (deposited or calculated lung dose) of at least about 30%, at least about 35%, at least about 40%, at least about 45%, at least about 50%, at least about 55%, at least about 60%, about 30% to about 60%, about 30% to about 55%, about 30% to about 50%, about 30% to about 40%, about 30% to about 90%, about 40% to about 80%, about 50% to about 60%, or about 60% to about 70% based on the nominal dose of the muscarinic antagonist (optionally in combination with a beta 2-adrenoceptor agonist) administered to the patient. In some embodiments, the high efficiency nebulizer achieves a respirable dose delivery rate (RDDR) of at least about 2 times, at least about 3 times or at least about 4 times the RDDR achievable with a conventional nebulizer. In some embodiments where the muscarinic antagonist is glycopyrrolate the RDDR is at least about 100 μg/min, at least about 150 μg/min, at least about 200 μg/min, about 100 μg/min to at least about 5,000 μg/min, about 150 μg/min to about 4,000 μg/min or about 200 μg/min to about 3,500 μg/min. In some embodiments, Wherein the muscarinic antagonist is glycopyrrolate, the high efficiency nebulizer achieves an output rate of at least about 120 μg/min, at least about 150 μg/min, at least about 200 μg/min or at least about 200 μg/min to at least about 5,000 μg/min, in some embodiments, the high efficiency nebulizer provides a respirable fraction (RF) of muscarinic antagonist of at least about 60%, at least about 65%, at least about 70%, at least about 75%, at least about 80%, at least about 85%, at least about 90%, about 60% to about 95%, about 65% to about 95%, about 65% to about 90% or about 70% to about 90%. In some embodiments, the high efficiency nebulizer provides a Geometric Standard Deviation (GSD) of emitted droplet size distribution of the solution administered with a high efficiency nebulizer of about 1.1 to about 2.1, about 1.2 to about 2.0, about 1.3 to about 1.9, at least about 1.4 to about 1.8, at least about 1.5 to about 1.7, about 1.4, about 1.5, or about 1.6. In some embodiments, administration of the muscarinic antagonist with the high efficiency nebulizer provides a Mass Median Aerodynamic Diameter (MMAD) of droplet size of the solution emitted with the high efficiency nebulizer of about 1 μm to about 5 μm, about 2 to about 4 μm, about 3 μm to about 4 μm, about 3 to about 4 μm, or about 3.5 to about 4.0 μm. In some particular embodiments, the high efficiency nebulizer provides droplets having a particular combination of MMAD and GSD, for example: an MMAD of less than about 5 μm and a GSD of about 1.1 to about 2.1; an MMAD of less than about 4.5 μm and a GSD of about 1.1 to about 2.1; an MMAD of about 1 μm to about 5 μm and a GSD of about 1.1 to about 2.1; an MMAD of about 1.5 to about 4.5 μm and a GSD of about 1.1 to about 2.1; an MMAD of less than about 5 μm and a GSD of about 1.1 to about 2.0; an MMAD of less than about 4.5 μm and a GSD of about 1.1 to about 2.0; an MMAD of about 1 μm to about 5 μm and a GSD of about 1.1 to about 2.0; an MMAD of about 1.5 to about 4.5 μm and a GSD of about 1.1 to about 2.0; an MMAD of less than about 5 μm and a GSD of about 1.1 to about 1.9; an MMAD of less than about 4.5 μm and a GSD of about 1.1 to about 1.9; an MMAD of about 1 μm to about 5 μm and a GSD of about 1.1 to about 1.9; an MMAD of about 1.5 to about 4.5 and a GSD of about 1.1 to about 1.9; an MAD of less than about 5 μm and a GSD of about 1.1 to about 1.8; an MMAD of less than about 4.5 μm and a GSD of about 1.1 to about 1.8; an MMAD of about 1 μm to about 5 μm and a GSD of about 1.1 to about 1.8; or an MMAD of about 1.5 to about 4.5 μm and a GSD of about 1.1 to about 1.8.

In some embodiment, the high efficiency nebulizer provides muscarinic antagonist lung deposition (deposited or calculated lung dose) of at least about 15%, at least about 20%, at least about 25%, at least about 30%, at least about 35%, at least about 40%, at least about 45%, at least about 50%, at least about 55%, at least about 60%, about 20% to about 40%, about 25% to about 35%, about 25 to about 30%, about 35% to about 90%, about 40% to about 80%, about 50% to about 60%, or about 60% to about 70% based on the nominal dose of the muscarinic antagonist. In some embodiments, the high efficiency nebulizer provides for one or more of (a) or (b); and one or more of (i), (ii), (iii) or (iv): (a) a respirable dose delivery rate (RDDR) of at least about 2 times, 3 times or 4 times the RDDR achievable with a conventional nebulizer (for example, where the muscarinic antagonist is glycopyrrolate, in some embodiments, RDDR is at least about 100 μg/min, at least about 150 μg/min, at least about 200 μg/min, about 100 μg/min to about 5,000 μg/min, about 150 μg/min to about 4,000 μg/min or about 200 μg/min to about 3,500 μg/min); (b) an output rate of muscarinic antagonist of at least about 2 times, 3 times or 4 times the output rate achievable with a conventional nebulizer (for example, where the muscarinic antagonist is glycopyrrolate, the output rate is at least about 120 μg/min, at least about 150 μg/min, at least about 200 μg/min or at least about 200 μg/min to about 5,000 μg/min); (i) a respirable fraction (RE) of muscarinic antagonist of at least about 30%, at least about 35%, at least about 40%, at least about 45%, at least about 50%, at least about 55%, at least about 65% to at least about 75% or at least about 75% to at least about 85% respirable fraction upon administration; (ii) a Geometric Standard. Deviation (GSD) of emitted droplet size distribution of the solution administered with a inhalation device of about (iii) about 1.1 to about 2.1, about 1.2 to about 2.0, about 1.3 to about 1.9, about 1.4 to about 1.8, about 1.5 to about 1.7, about 1.4, about 1.5, or about 1.6; (iv) or a Mass Median Aerodynamic Diameter (MMAD) of droplet size of the solution emitted with the inhalation device of about 1 μm to about 5 μm, about 2 to about 4 μm, about 3 to about 4 μm, or about 3.5 to about 4.0 μm.

In accordance with the invention, in some embodiments, a high efficiency nebulizer may be adapted or adaptable to operate in conjunction with a unit dosage form, such as an ampule or vial, which contains a single dose of a muscarinic antagonist composition for the treatment of COPD. The unit dosage form comprises a container that contains an inhalation solution comprising the muscarinic antagonist, such as glycopyrrolate. The container is adapted to cooperate with the high efficiency nebulizer device in such a way as to permit administration of the nominal dose of the inhalation solution to a patient. In some embodiments, the high efficiency nebulizer and the unit dosage form are configured so that they are useable together, but not with other devices or dosage forms. In some particular embodiments, the unit dosage form is configured such that it fits into a keyhole-like structure in the high efficiency nebulizer, but will not operate with other nebulizer devices. In such embodiments, the high efficiency nebulizer is configured such that it will accept and properly operate with the unit dosage form containing the muscarinic antagonist, but not with other dosage forms.

Additional features of a high efficiency nebulizer with perforated membranes are disclosed in U.S. Pat. Nos. 6,962, 151, 5,152,456, 5,261,601, and 5,518,179, each of which is hereby incorporated by reference in its entirety. Other embodiments of the high efficiency nebulizer contain oscillatable membranes. Features of these high efficiency nebulizers are disclosed in U.S. Pat. Nos. 7,252,085; 7,059,320; 6,983,747, each of which is hereby incorporated by reference in its entirety.

Commercial high efficiency nebulizers are available from: PARI (Germany) under the trade name eFlow®; Aerogen, Ltd. (Ireland) under the trade names AeroNeb® Go and AeroNeb® Pro, AeroNeb® Solo, and other nebulizers utilizing the OnQ® nebulizer technology; Respironics (Murrysville, Calif.) under the trade names I-Neb®; Omron (Bannockburn, Ill.) under the trade name Micro-Air®; Activaero (Germany) under the trade name Akita®, and AerovectRx (Atlanta, Ga.) under the trade name AerovectRx®. Other high efficiency nebulizers are contemplated within the scope of this disclosure; and the recitation of particular high efficiency nebulizers is not intended to exclude other high efficiency nebulizers from the scope of the invention.

Conventional Nebulizers

Conventional nebulizers include, for example jet nebulizers or ultrasonic nebulizers. Jet nebulizers generally utilize compressors to generate compressed air, which breaks the liquid medication into small breathable droplets, which form an aerosolized (atomized) mist. In some of these embodiments, when the patient breathes in, a valve at the top opens, which then allows air into the apparatus, thereby speeding up the mist generation; when the patient breathes out, the top valve closes, thereby slowing down the mist generation while simultaneously permitting the patient to breathe out through the opening of a mouthpiece flap.

In general, conventional nebulizers are characterized by relatively low efficiency in delivery of a muscarinic antagonist to the lung. Thus, a conventional nebulizer, such as a jet nebulizer, is characterized by one or more of the following: (1) about 20% or less calculated respirable dose or measured deposited lung dose as a percentage of the nominal dose of API administered to the patient; (2) a respirable dose delivery rate (RDDR) of less than about 100 μg/min of the muscarinic antagonist, when glycopyrrolate, administered to the patient; (3) an output rate of less than about 100 μg/min of glycopyrrolate administered to the patient; (4) a residual volume of greater than about 10% of the nominal dose of the muscarinic antagonist.

Some conventional nebulizers are disclosed in U.S. Pat. Nos. 6,513,727, 6,513,519, 6,176,237, 6,085,741, 6,000, 394, 5,957,389, 5,740,966, 5,549,102, 5,461,695, 5,458,136, 5,312,046, 5,309,900, 5,280,784, and 4,496,086, each of which is hereby incorporated by reference in its entirety.

Commercial conventional nebulizers are available from: PARI (Germany) under the trade names PARI LC Plus®, LC Star®, and PARI-Jet®, A & H Products, Inc. (Tulsa, Okla.) under the trade name AquaTower®; Hudson RCI (Temecula, Calif.) under the trade name AVA-NEB®; Intersurgical, Inc. (Liverpool, N.Y.) under the trade name Cirrus®; Salter Labs (Arvin, Calif.) under the trade name Salter 8900®; Respironics (Murrysville, Pa.) under the trade name Sidestream®, Bunnell (Salt Lake City, Utah) under the trade name Whisper Jet®; Smiths-Medical (Hyth Kent, UK)

under the trade name Downdraft®, and DeVilbiss (Somerset, Pa.) under the trade name DeVilbiss®.

Active Ingredient(s)

Muscarinic Antagonists

Acetylcholine released from cholinergic neurons in the peripheral and central nervous systems affects many different biological processes through interaction with two major classes of acetylcholine receptors: the nicotinic and the muscarinic receptors.

Muscarinic acetylcholine receptors are widely distributed in vertebrate organs where they mediate many vital functions. Three subtypes of muscarinic acetylcholine receptors have been identified as important in the lung, M1, M2, and M3, each with its unique pharmacological properties and a product of a distinct gene. These three subtypes are also located in organs other than the lung.

In the lung, M3 muscarinic receptors mediate smooth muscle contraction. Stimulation of M3 muscarinic receptors activate the enzyme phospholipase C via binding of the stimulatory G protein Gq/11 (Gs), leading to liberation of phosphatidyl inositol-4, 5-bisphosphate, resulting in phosphorylation of contractile proteins and bronchial constriction. M3 muscarinic receptors are also found on pulmonary submucosal glands, Stimulation of this population of M3 muscarinic receptors results in mucus secretion. M2 muscarinic receptors make up approximately 50-80% of the cholinergic receptor population on airway smooth muscles. Under normal physiological conditions, M2 muscarinic receptors provide tight control of acetylcholine release from parasympathetic nerves. M1 muscarinic receptors are found in the pulmonary parasympathetic ganglia where they function to enhance neurotransmission.

Muscarinic acetylcholine receptor dysfunction in the lungs has been noted in a variety of different pathophysiological states. In COPD patients, inflammatory conditions lead to loss of inhibitory M2 and M3 muscarinic acetylcholine autoreceptor function on parasympathetic nerves supplying the pulmonary smooth muscle, causing an increased release of acetylcholine. This dysfunction in muscarinic receptors results in airway hyperreactivity and hyperresponsiveness.

Muscarinic acetylcholine receptor antagonist agents, or muscarinic antagonists, have the ability to inhibit the action of the neurotransmitter acetylcholine by blocking its interaction with muscarinic cholinergic receptors in general, and its interaction with specific muscarinic receptor subtypes in particular. Muscarinic antagonists thereby prevent the effects resulting from the passage of unnecessary impulses through the parasympathetic nerves mediated by increased stimulation in patients with dysfunctional receptors, resulting in, among other physiological effects, relaxation of smooth muscles in the lung.

Aclidinium, ((3R-3-{[hydroxydi(thiophen-2-yl)acetyl]oxy}-1-(3-phenoxypropyl)-1-azoniabicyclo[2.2.2]octane bromide), is a specific long-acting muscarinic receptor antagonist. Aclidinium is in development for use as an anticholinergic agent. Clinically, aclidinium has been tested in a dry powder inhaled format.

In some embodiments of the present invention, the muscarinic antagonist is aclidinium and is administered at a nominal dosage of 100 µg/dose to about 5 mg/dose, about 50 µg/dose to about 2 mg/dose or about 50 µg/dose to about 1 mg per dose. In other embodiments, aclidinium is given in 100 µg, 200 µg, 300 µg, 400 µg, 500 µg, 600 µg, 700 µg, 800 µg, 900 µg, or 1,000 µg doses.

The process of making aclidinium is known by a person of ordinary skill in the art. Aclidinium can be made by a number of known methods including those described in U.S. Pat. No. 6,750,226, which is incorporated herein by reference in its entirety, and which sets forth several structurally related muscarinic antagonists. Additional examples of muscarinic antagonists are set forth in U.S. Pat. Nos. 7,312,231 and 7,208,501, each of which is incorporated herein by reference in its entirety.

Trospium (endo-3-[(Hydroxydiphenylacetyl)oxy]spiro[8-azoniabicyclo[3.2.1]ocatane-8,1'-pyrrolidinium] chloride benzilate), is a specific long-acting muscarinic; receptor antagonist. Trospium has been known for many years to be an effective anticholinergic agent. Clinically, trospium has been used in several indications and been delivered by a number of different routes. Currently, trospium is used as a urinary antispasmotic and is sold under the brand name Sanctura®.

In some embodiments of the present invention, the muscarinic antagonist is trospium and is administered at a nominal dosage of 10 µg/dose to about 5 mg/dose, about 10 µg/dose to about 2 mg/dose or about 50 µg/dose to about 1 mg per dose. In other embodiments, trospium is given in 10 µg, 50 µg, 100 µg, 200 µg, 300 µg, 400 µg, 500 µg, 600 µg, 700 µg, 800 µg, 900 µg, or 1,000 µg doses.

The process of making trospium is known by a person of ordinary skill in the art. Trospium can be made by a number of known methods including those described in U.S. Pat. No. 3,480,626, which is incorporated herein by reference in its entirety.

Glycopyrrolate, 3-[(cyclopentylhydroxyphenylacetyl)oxy]-1,1-dimethylpyrrolidinium, is a specific long-acting muscarinic receptor antagonist. Glycopyrrolate has been known for many years to be an effective anticholinergic agent. Clinically, glycopyrrolate has been used in several indications and been delivered by a number of different routes. Currently, glycopyrrolate is approved for use as an injectable compound to reduce secretions during anesthesia and also as an oral product for treating gastric ulcers.

In some embodiments of the present invention, the muscarinic antagonist is glycopyrrolate and is administered with a high efficiency nebulizer at a nominal dosage of about 25 µg/dose to about 1 mg/dose, about 25 pig/dose to about 0.5 mg/dose, about 25 µg/dose to about 400 µg/dose, about 25 µg/dose to about 300 µg/dose, about 25 µg/dose to about 200 µg/dose, about 25 µg/dose to about 150 µg/dose, about 25 µg/dose to about 125 µg/dose, about 25 µg/dose to about 100 µg/dose 50 µg/dose to about 1 mg/dose, about 50 µg/dose to about 0.5 mg/dose, about 50 µg/dose to about 300 µg/dose, about 50 µg/dose to about 250 µg/dose, about 50 µg/dose to about 200 µg/dose, about 50 µg/dose to about 150 µg/dose, about 50 µg/dose to about 125 µg/dose, about 50 µg/dose to about 100 µg/dose, less than about 150 µg/dose, less than about 100 µg/dose, equal to or less than about 80 µg/dose, 100 µg/dose to about 5 mg/dose, about 200 µg/dose to about 2 mg/dose or about 250 µg/dose to about 1 mg per dose. In some preferred embodiments, the muscarinic antagonist is glycopyrrolate and is administered with a high efficiency nebulizer at a nominal dosage of about 25 µg, about 30 µg, about 35 µg, about 40 µg, about 45 µg, about 50 µg, about 55 µg, about 60 µg, about 65 µg, about 70 µg, about 75 µg, about 80 µg, about 85 µg, about 90 µg, about 95 µg, about 100 µg, about 110 µg, about 120 µg, about 125 µg, about 130 µg, about 135 µg, about 140 µg, about 150 µg, about 160 µg, about 170 µg, about 175 µg, about 180 µg, about 190 µg, about 200 µg, about 25 µg to about 500 µg, about 50 µg to about 500 µg, about 50 µg to about 300 µg, about 50 µg to about 250 µg, about 50 µg to about 200 µg, about 50 µg, about 75 µg, about 100 µg, about 125 µg, about 150 µg, about 175 µg, about 200 µg, about 225 µg, about 250 µg, about 275 µg or about 300 µg of glycopyrrolate per dose, in some preferred embodiments, administration of the nominal dose of glycopyrrolate with a high efficiency nebulizer produces clinically meaningful improvement in lung function in a COPD patient at least 24 hours after administration of a single dose.

The process of making glycopyrrolate is known by a person of ordinary skill in the art. Glycopyrrolate can be made as follows. First, alpha-phenylcyciopentaneglycolic acid is esterified by refluxing with methanol in the presence of hydrochloric acid and the resulting ester is transesterified with 1-methyl-3-pyrrolidinol using sodium as a catalyst; the transester is then reacted with methyl bromide to give glycopyrrolate. U.S. Pat. No. 6,433,003, which describes this process in more detail, is hereby incorporated by reference in its entirety.

Glycopyrrolate for injectable and oral administration is readily commercially available. Injectable glycopyrrolate in commercial administrations are sold by: Baxter Healthcare, Inc. (Deerfield, Ill.) under the trade name Robinul and by Luitpold Pharmaceuticals, Inc. (Shirley, N.Y.) under the generic name glycopyrrolate, Oral glycopyrrolate is commercially available under the generic name glycopyrrolate from Corepharma, LLC (Middlesex, N.J.) and Kali Laboratories, Inc. (Somerset, N.J.), and is available from Sciele Pharma, Inc. (Atlanta, Ga.) under the trade names Robinul and Robinul Forte.

Tiotropium is another long-acting muscarinic antagonist that may be mentioned. In some embodiments, the dose of tiotropium administered with a high efficiency nebulizer will be less than about 15 µg, less than about 12 µg, less than about 10 µg or less than about 8 µg. In some embodiments, the dose will be in a range of about 1-10 µg, about 1-9 µg, about 1-8 µg or about 1-5 µg about 1 µg, about 2 µg, about 3 µg, about 4 µg, about 5 µg, about 6 µg, about 7 µg, about 8 µg, about 9 µg or about 10 µg per dose.

Muscarinic antagonists can be long-acting or short-acting. Long-acting muscarinic antagonists have a therapeutic effect lasting greater than about 6 hours. Short-acting muscarinic antagonists have a duration of therapeutic effect of less than about 6 hours. Long-acting muscarinic antagonists include, but are not limited to, glycopyrrolate, tiotropium, aclidinium, trospium, QAT370, GSK233705, GSK656398, BEA 2180, or a pharmaceutical acceptable derivative, salt, enantiomer, diastereomer, or racemic mixtures thereof.

Short-acting muscarinic antagonists include, but are not limited to ipratropium, oxitropium or a pharmaceutical acceptable derivative, salt, enantiomer, diastereomer, or racemic mixtures thereof.

In some embodiments, the muscarinic antagonist is glycopyrrolate, tiotropium, aclidinium, trospium, QAT370, GSK233705, GSK 656398, BEA2180, ipratropium, oxitropium, oxybutynin or a pharmaceutical acceptable derivative, salt, enantiomer, diastereomer, or a pharmaceutical acceptable derivative, salt, enantiomer, diastereomer, or racemic mixture thereof.

In some embodiments, the inhalation solution comprising the muscarinic antagonist(s) further comprises a corticosteroid, such as fluticasone, mometasone, beclomethasone, triamcinolone, fluniolide, ciclesonide, or budesonide. In some embodiments, the inhalation solution further comprises an excipient, including an organic acid, such as citric acid, ascorbic acid or optionally a combination of both, pilocarpine, cevimeline or carboxymethylcellulose, or a mucolytic compound. In some embodiments, the inhalation solution contains muscarinic antagonist (such as glycopyrrolate) a beta 2-adrenoceptor agonist and/or a corticosteroid or non-steroidal anti-inflammatory.

Beta 2-Adrenoceptor Agonises

The stimulation of beta 2-adrenergic receptors stimulate adenylate cyclase, resulting in an increased level of the second messenger cAMP that in turn leads to decreased intracellular calcium concentration and consequently smooth muscle relaxation. Stimulation of certain beta 2-adrenoceptor receptors in particular causes hydrolysis of polyphosphoinositides and mobilization of intracellular calcium which results in a variety of calcium mediated responses such as smooth muscle contraction. Consequently, inhibition of this receptor activation prevents the intracellular calcium increase and leads to smooth muscle relaxation.

Beta 2-adrenoceptor agonists can be long-acting or short-acting. Long-acting beta 2-adrenoceptor agonists (LABAs) have a therapeutic effect lasting greater than about 6 hours. Short-acting beta 2-adrenoceptor agonists (SABAs) have a duration of therapeutic effect of less than about 6 hours.

Compounds having beta 2-adrenoceptor agonist activity with a long-acting or short-acting effect have been developed to treat respiratory conditions. Such compounds include, but are not limited to, albuterol; bambuterol; bitoiterol; broxaterol; carbuterol; clenbuterol; ibuterol; sulfonterol; isoproterenol; trimetoquinol; formoterol; desformoterol; hexoprcnaline; ibuterol; indaeaterol; isoetharine; isoprenaline; isoproterenol; levalbuterol; metaproterenol; picumeterol; pirbuterol; procaterol; reproterol; rimiterol; salbutamol, salmeterol; sulfonterol; terbutaline; trimetoquinol; tulobuterol; and TA-2005 (8-hydroxy-5-((1R)-1-hydroxy-2-(N-((1R)-2-(4-methoxyphenyl)-1-methylethyl) amino)ethyl)-carbostyril hydrochloride); or a or a pharmaceutical acceptable derivative, salt, enantiomer, diasteriomer, or racemic mixtures thereof.

Formoterol is a long-acting beta 2-adrenoceptor compound. The process of making formoterol is known by one of skill in the art. Formoterol is derived from adrenaline and is used as a beta 2-adrenoceptor agonist in inhalation therapy of respiratory diseases. Formoterol has been formulated as a dry powder and administered via devices such as the Turbuhaler® and the Aerolizer®.

Formoterol is also available as a tablet and a dry syrup in certain areas of the world (e.g., Atock®, marketed by Yamanouchi Pharmaceutical Co. Ltd., Japan). Formoterol administrations are also available in other areas (e.g., Europe and U.S.) for propellant-based metered dose inhalers and dry powder inhalers (e.g., Turbuhaler®, Aerolizer.® and Foradil Aerolizer®). None of these administrations are water based solutions.

Commercial administrations of arformoterol tartrate (formoterol) are sold by Sepracor, Inc, (Marlborough, Mass.) under the trade name Brovana®. Formoterol fumarate is sold by several companies including AstraZeneca, Inc. (London, England) under the trade name Symbicort®, Novartis International AG (Basel, Switzerland) under the trade names Foradir and Certihaler®, and Dey, L.P. (Napa, Calif.) under the trade name Perforomist®.

Salmeterol is a long-acting beta 2-adrenoceptor compound. The process for making salmeterol is known by a person of ordinary skill in the art and is described in U.S. Pat. No. 4,992,474, which is hereby incorporated by reference. Commercial administrations of salmeterol are sold by GlaxoSmithKline, Inc. (Triangle Park, N.C.) under the trade names Advair® and Serevent®.

Inhalation Solutions

The present invention relates to methods and inhalation systems for the use of inhalation solutions in an inhalation device for the treatment or prophylaxis of a respiratory condition in a patient, such as COPD, chronic bronchitis, or emphysema. In some embodiments, the methods and inhalation systems comprise administering to the patient a nominal dose of one or more API, for example muscarinic antagonist (optionally in combination with a beta 2-adrenoceptor agonist and/or a corticosteroid) in an aqueous inhalation solution with an inhalation device, e.g. a high efficiency nebulizer, conventional nebulizer, and optionally a conventional inhalation device.

In some embodiments, an aqueous inhalation solution containing glycopyrrolate is administered with a high efficiency nebulizer at a concentration greater than about 0.5 mg/mL. In some embodiments, an aqueous inhalation solution containing glycopyrrolate is administered with a high efficiency nebulizer at a concentration of 0.05 mg/mL to about 2.0 mg/mL, at least about 0.05 mg/mL, at least about 0.5 mg/mL, at least about 1.0 mg/mL to about 2.0 mg/mL, at least about 0.25 mg/mL, at least about 0.5 mg/mL, at least about 1.0 mg/mL, at least about 1.5 mg/mL, or at least about 2.0 mg/mL, Without wishing to be bound by theory, it is believed that the higher concentration of muscarinic antagonist, for example glycopyrrolate, results in saturation and/or targeting of a greater number of muscarinic receptors with the muscarinic antagonist and/or targeting of the muscarinic receptors with the muscarinic antagonist for a greater period of time. In some embodiments, it is believed that administration of a muscarinic antagonist, such as glycopyrrolate, at a concentration of at least about 100 to about 300 μg/mL will result in greater duration and/or magnitude of therapeutic effect. Without wishing to be bound by theory, it is believed that the higher concentration of muscarinic antagonist, for example glycopyrrolate, coupled with the improved delivery and/or lung distribution achievable with a high efficiency nebulizer, results in saturation and/or targeting of a greater number of muscarinic receptors with the muscarinic antagonist and/or targeting of the muscarinic receptors with the muscarinic antagonist for a greater period of time. In some embodiments, it is believed that administration of a muscarinic antagonist, such as glycopyrrolate, in a nebulized form having an MMAD of less than about 4 μm and a GSD of less than about 1.8, wherein the loaded dose has a concentration greater than 0.25 mg/mL, will result in greater duration and/or magnitude of therapeutic effect. Without wishing to be bound by theory, it is believed that this combination of characteristics results in saturation and/or targeting of a greater number of muscarinic receptors with the muscarinic antagonist and/or targeting of the muscarinic receptors for a greater period of time.

In some embodiments, the methods, devices and systems employ an aqueous inhalation solution containing glycopyrrolate, at an administration of about 25 μg/dose to about 1 mg/dose, about 25 μg/dose to about 500 μg/dose, about 25 μg/dose to about 400 μg/dose, about 25 μg/dose to about 250 μg/dose, about 50 μg/dose to about 1 mg/dose, about 50 μg/dose to about 500 μg/dose, about 50 μg/dose to about 400 μg/dose, about 50 μg/dose to about 250 μg/dose, about 25 μg/dose to about 5 mg/dose, about 200 μg/dose to about 2 mg/dose, or about 250 μg/dose to about 1 mg per dose. In some embodiments, the methods, devices and systems comprise a composition containing glycopyrrolate in an amount of about 50 μg/dose to about 1 mg/dose, about 50 μg/dose to about 0.5 mg/dose, about 50 μg/dose to about 250 μg/dose, about 50 μg/dose to about 150 μg/dose, about 50 μg/dose to about 125 μg/dose, about 50 μg/dose to about 100 μg/dose, less than about 150 μg/dose, less than about 100 μg/dose, equal to or less than about 80 μg/dose, 100 μg/dose to about 5 mg/dose, about 200 μg/dose to about 2 tug/dose or about 250 μg/dose to about 1 mg per dose.

In some embodiments, the aqueous inhalation solution is administered with an inhalation device, e.g. high efficiency nebulizer, at a fill volume of about 0.1 to about 1.0 mL, e.g. about 0.3 to about 0.7 mL. In some embodiments, the fill volume is less than about 0.5 mL, at least about 0.5 mL, to about 1.5 mL, at least about 0.25 mL or less, at least about 0.5 mL to about 1.5 mL, at least about 1.5 mL, or at least about 2.0 mL. In some embodiments, the aqueous inhalation solution is administered with an inhalation device, e.g. high efficiency nebulizer, at a fill volume of at least about 0.25 mL to about 2.0 mL, about 0.5 mL to about 1.5 mL, about 0.5 mL to about 1.0 mL, about 0.5 mL or less, about 1 mL or less, about 1.5 mL or less, or about 2.0 mL or less. In some embodiments, the aqueous inhalation solution is administered with an inhalation device, e.g. high efficiency nebulizer, which provides for a residual volume of muscarinic antagonist after administration of the muscarinic antagonist of less than about 10%, less than about 5%, or less than about 3% of the nominal dose.

In some embodiments, the aqueous inhalation solution is administered in about 0.25 to about 10 minutes, about 0.50 to about 8 minutes, less than about 8, less than about 7, less than about 6, less than about 5, less than about 4, less than about 3, less than about 2, less than about 1.75 minutes, or less than about 1.5 minutes. In some embodiments, the aqueous inhalation solution is administered in about 3 minutes or less.

In some embodiments, a muscarinic antagonist is co-administered with a beta 2-adrenoceptor agonist in the aqueous inhalation solution. In some embodiments, the beta 2-adrenoceptor agonist is a long-acting beta agonist (LABA). In some embodiments, the beta 2-adrenoceptor agonist is a short-acting beta agonist (SABA). In some embodiments, the beta 2-adrenoceptor agonist is either a SABA or a LAMA.

In some embodiments, the nominal, dose administered with the high efficiency nebulizer is a muscarinic antagonist (optionally in combination with a beta 2-adrenoceptor agonist and/or corticosteroid or non-steroidal anti-inflammatory) that is substantially free of preservative, such as benzyl alcohol. In some embodiments, the nominal dose of muscarinic antagonist (optionally in combination with a beta 2-adrenoceptor agonist and/or corticosteroid or non-steroidal anti-inflammatory) is in an inhalation solution that further comprises at least one excipient or active pharmaceutical ingredient. In some embodiments, the excipient or active ingredient is a member of the group consisting of organic acid (such as a low molecular weight organic acid like citric acid or ascorbic acid), an antioxidant (such as EDTA), an osmolarity adjusting agent (such as a salt like sodium chloride) or a pH buffer.

In some embodiments, the inhalation solution comprising the muscarinic antagonist(s) further comprises a corticosteroid, such as fluticasone, mometasone, beclomethasone, triamcinolone, fluniolide, ciclesonide, or budesonide. In some embodiments, the inhalation solution further comprises an excipient or an active pharmaceutical ingredient. In some embodiments, the excipient or active pharmaceutical ingredient is an organic acid (such as citric acid, ascorbic acid, or both), pilocarpine, cevimeline, carboxymethylcellulose, or a mucolytic compound.

Characterization of Inhalation Devices

The efficiency of a particular inhalation device can be measured in many different ways, including an analysis of pharmacokinetic properties, measurement of lung deposition (deposited lung dose), measurement of respirable dose delivery rates (RDDR), a determination of output rates, respirable fraction (RF), geometric standard deviation (GSD), mass median aerodynamic diameter (MMAD), and mass median diameter (MMD) among others.

A person skilled in the art is knowledgeable of methods and systems for examining a particular inhalation device. One such system consists of a computer and a hollow cylinder in a pump with a connecting piece to which an inhalation device is to be connected. In the pump there is a piston rod, which extends out of the hollow cylinder. A linear drive unit can be activated in such a manner that one or more breathing pattern will be simulated on the connecting piece of the pump. In order to be able to carry out the evaluation of the inhalation device, the computer is connected in an advantageous configuration with a data transmission. With the aid of the data transmission, the computer can be connected with another computer with specific data banks, in order to exchange the data of breathing patterns. In this manner, a breathing pattern library which is as representative as possible can be very rapidly formed. U.S. Pat. No. 6,106,479 discloses this method for examining an inhalation device in more detail, and is hereby incorporated by reference in its entirety.

Pharmacokinetic Profile

Pharmacokinetics is concerned with the uptake, distribution, metabolism and excretion of a drug substance. A pharmacokinetic profile comprises one or more biological measurements designed to measure the absorption, distribution, metabolism and excretion of a drug substance. One way of visualizing a pharmacokinetic profile is by means of a blood plasma concentration curve, which is a graph depicting mean active ingredient blood plasma concentration on the Y-axis and time (usually in hours) on the X-axis. Some pharmacokinetic parameters that may be visualized by means of a blood plasma concentration curve include:

$AUC_{(0-t)}$: The area under the curve from time zero to time of last measurable concentration.
$AUC_{(0-\infty)}$: The total area under the curve.
$C_{max}$: The maximum plasma concentration in a patient.
$T_{max}$: The time to reach maximum plasma concentration in a patient
T1/2: The elimination half life.

An enhanced pharmacokinetic profile in a patient can be indicated by an increased $AUC_{(0-t)}$, $AUC_{(0-\infty)}$, $C_{max}$, T1/2, or $T_{max}$ or an increased slope in the plasma concentration curve within the first hour after treatment. Enhanced levels of a pharmaceutical agent in the blood plasma of a patient may result in one or more improved symptoms of an airway respiratory condition, e.g. COPD.

In some embodiments, a method or system described herein provides at least about a two-fold enhancement in pharmacokinetic profile, meaning that administration of an active pharmaceutical ingredient ("API"—e.g. a muscarinic antagonist, optionally in combination with a beta 2-adrenergic agonist) with a high efficiency nebulizer provides at least about a two-fold increase in one or more of $AUC_{last}$, $AUC_{(0-\infty)}$ or $C_{max}$ as compared to the same or lower nominal dose of API administered with a conventional nebulizer.

In some embodiments, a method or system described herein provides at least about a two-fold enhancement in pharmacokinetic profile, meaning that administration of an active pharmaceutical ingredient ("API"—e.g. a muscarinic antagonist, optionally in combination with a beta 2-adrenergic agonist) with a high efficiency nebulizer provides at least about a 1.8-fold increase in one or more of $AUC_{last}$, $AUC_{(0-\infty)}$, or $C_{max}$ as compared to the same or lower nominal dose of API administered with a conventional nebulizer.

In some embodiments, a method or system described herein provides at least about a two-fold enhancement in pharmacokinetic profile, meaning that administration of an active pharmaceutical ingredient ("API"—e.g. a muscarinic antagonist, optionally in combination with a beta 2-adrenergic agonist) with a high efficiency nebulizer provides at least about a 1.5-fold increase in one or more of $AUC_{last}$, $AUC_{(0-\infty)}$ or $C_{max}$ as compared to the same or lower nominal dose of API administered with a conventional nebulizer.

In some embodiments, a method or system described herein provides at least about a two-fold enhancement in pharmacokinetic profile, meaning that administration of an active pharmaceutical ingredient ("API"—e.g. a muscarinic antagonist, optionally in combination with a beta 2-adrenergic agonist) with a high efficiency nebulizer provides a comparable $AUC_{last}$, $AUC_{(0-\infty)}$, or $C_{max}$ as compared to the same or lower nominal dose of API administered with a conventional nebulizer.

Enhanced Therapeutic Effect

The assessment of therapeutic effect is known to those skilled in the art, such as pulmonologists trained to recognize the distinctions between various types of respiratory illnesses, including chronic obstructive airway disease ("COPD") and asthma. Assessment of efficacy may be carried out by various methods known to the person skilled in the art, and may include both objective and subjective (patient-generated) measures of efficacy. Objective measures of efficacy can be obtained inter aria by spirometry; and subjective measures of efficacy can be obtained for example by employing one or more patient symptom questionnaires or surveys. In some embodiments, the methods and systems herein are for treatment of COPD, and thus such embodiments are discussed in further detail below. It is considered that embodiments of the methods and symptoms described herein. (including those employing administration of muscarinic antagonist, optionally in combination with a beta 2-adrenoceptor agonist and/or a corticosteroid, with a high efficiency nebulizer or at a high concentration) will provide superior efficacy in treatment of COPD as compared to treatment with conventional methods (such as those in which muscarinic antagonist is administered with a conventional nebulizer and/or at a lower concentration).

COPD Efficacy Assessment

COPD is a progressive, chronic disease of the airways, characterized by chronic inflammation and destruction of the airways and lung parenchyma, resulting in airflow obstruction. Thus, efficacy in the treatment of COPD refers to the ability to restore airflow to the patient. In some cases, especially in older and immune-compromised patients, COPD can be further characterized by exacerbations—acute, often pathogen- or allergen-induced, degradation of airflow. There are several indicators (endpoints) of efficacy in the treatment of COPD. Some efficacy endpoints that are used in COPD studies are set forth below. It is considered that a muscarinic antagonist will demonstrate efficacy in one or more of these tests. In particular, it is considered that in some embodiments a nominal dose of a muscarinic antagonist administered with a high efficiency nebulizer will outperform substantially the same or higher nominal dose of muscarinic antagonist administered with a conventional nebulizer, as determined by one or more of these endpoints.

Pulmonary function tests: Pulmonary function testing by spirometry is a useful way to assess airflow obstruction and, therefore, is a useful way to assess the efficacy of COPD treatment as well as to compare the relative merits of different COPD treatments e.g. administration of different dosages of active pharmaceutical ingredient ("API"), administration of substantially the same dosages of API with different delivery devices, or administration of different dosages of API with different delivery devices. Forced expiratory volume in one second ($FEV_1$) obtained from typical spirometry is commonly used as an efficacy endpoint because $FEV_1$ is a reflection of the extent of airway obstruction. Spirometry is also well-standardized, is easy to perform and provides consistent, reproducible results across different pulmonary function laboratories. Air-trapping and hyperinflation are common features in COPD, particularly in emphysema, and are reflected in parameters of lung function testing, such as an elevation in the residual volume to total lung capacity ratio (RV/TLC). Hyperinflation is believed to be responsible, at least in part, for the sense of dyspnea.

Outcome Measures can also be used, alone or preferably in combination with one or more objective tests, to determine efficacy of COPD therapy.

Exacerbation: The progressive course of COPD is often aggravated by periods of exacerbations generally defined as increased symptoms, particularly increasing cough, dyspnea and production of sputum over baseline that usually requires change in treatment. Exacerbations are mostly caused by bronchial infections and are the most frequent cause of medical visits, hospital admissions and death in patients with COPD. One of the main objectives of COPD treatment is to reduce the frequency and severity of exacerbations and the frequency of hospitalizations and duration of hospital stay. The characteristics, including the limitations, of these tests will be known to those skilled in the art.

Exercise capacity: Reduced capacity for exercise is a typical consequence of airflow obstruction in COPD patients, particularly because of dynamic hyperinflation occurring during exercise. Exercise testing provides useful assessment of the degree of lung impairment, prognosis and the effects of treatments. Assessment of exercise capacity by treadmill or cycle ergometry combined with lung volume assessment is in some cases a tool to assess efficacy of a COPD drug. Alternative assessments of exercise capacity, such as the Six Minute Walk or Shuttle Walk, can also be used in some cases. The characteristics, including the limitations, of these tests will be known to those skilled in the art.

Symptom Scores: Symptom scores determined by asking patients to evaluate specific symptoms on a categorical, visual or numerical scale can be a simple way to assess efficacy of a drug based on the patient's own assessment of health status. Symptom scores can be valuable for assessing efficacy of a drug specifically aimed at relieving a symptom. In clinical programs aimed at other aspects of COPD, patient-reported symptom scores can be useful in assessing secondary effects of the therapy and may provide important additional evidence of efficacy. The characteristics, including the limitations, of these tests will be known to those skilled in the art.

Activity Scales: Activity scales provide an assessment of the patient's severity of breathlessness and how activities of daily living influence the patient's breathlessness. Activity scales such as the Medical Research Council dyspnea score, the Borg Scale, and the Mahler Baseline Dyspnea Index/Transitional Dyspnea Index, can be used in some cases as supportive evidence of efficacy. These scales are relatively simple to administer. The characteristics, including the limitations, of these tests will be known to those skilled in the art.

Health-related, quality-of-life instruments: Health-related quality of life measurement provides a standardized assessment of the impact of the disease on patients' daily lives, activity and well-being. Health-related quality-of-life instruments, such as the St. George's Respiratory Questionnaire and the Chronic Respiratory Questionnaire, are designed to systematically assess many different aspects of the effect of COPD on a patient's life. These instruments can be used to assess efficacy of a drug. These instruments are multidimensional and assess various effects of the disease on a patient's life and health status. The characteristics, including the limitations, of these tests will be known to those skilled in the art.

Further information regarding testing drugs for efficacy in the treatment of COPD can be found in the United States Food and Drug Administration's guidance document entitled: "Guidance for Industry: Chronic Obstructive Pulmonary Disease: Developing Drugs for Treatment," November, 2007, which is available from www.fda.gov/cder/guidance/index.htm.

A muscarinic antagonist is said to have a therapeutic effect in the treatment of COPD (at a relevant time point) when it causes an increase in one or more measures of pulmonary function to a predetermined percentage above baseline. In some embodiments, the predetermined percentage above baseline is about 5%, about 10%, about 15%, about 20%, or about 25%. In some specific embodiments, a muscarinic antagonist will be considered to have a therapeutic effect when it raises one or more of the above-mentioned spirometry measurements (e.g. $FEV_1$) at least about 15% above baseline. In general, an improvement in pulmonary function (e.g. $FEV_1$) of 100 mL or 10% above baseline is considered clinically relevant; and an improvement in pulmonary function above baseline of 100 mL or 10% above baseline at 24 hours post dosing is considered clinically relevant for a CSI) (1× daily dosing) drug.

Spirometry is the measurement of respiration, which is generally conducted by a physician with the aid of a spirometer. Spirometers measure inspired and expired airflow for the purpose of assessing pulmonary ventilatory function. Spirometry is the most common pulmonary function test measuring lung function. Typical spirometers display volume-time curves (showing volume on the Y-axis and time, usually in seconds, on the X-axis) and optionally a flow-volume curves (showing rate of flow on the Y-axis and the total volume inspired/expired on the X-axis). U.S. Pat. No. 7,291,115 discloses a spirometer and method to measure the ventilatory function by spirometry, and is hereby incorporated by reference in its entirety. Methods of using a spirometer are familiar to those skill in the art.

Relevant parameters measured by spirometers include:

FEV1 (or $FEV_1$): Forced Expiratory Volume in 1 Second, which is the maximum volume of air exhaled during the first second of maximum effort from a maximum inhalation. It is expressed in units of volume (e.g. liters (L)), especially as volume change from baseline or placebo, and/or in percentage change in $FEV_1$ from baseline or placebo. It becomes altered in cases of bronchial obstruction and it is fundamental for diagnosing and monitoring obstructive diseases, e.g. COPD.

Change in $FEV_1$: Change in $FEV_1$ may be calculated as the difference between the $FEV_1$ value measured after dosing and the $FEV_1$ measured immediately prior to dosing. Change in $FEV_1$ may also be measured in reference to a placebo. These values may be expressed in absolute terms or in terms of percent change from baseline or placebo.

$FEV_1$ AUC: This is the area between the FEV1 measurements vs. time curve (relative to baseline and/or placebo) over a time course. In some embodiments, the time course is a predetermined period, such as 12 hr., 18 hr., 24 hr., 30 hr., or 36 hr. $FEV_1AUC$ (e.g. relative to baseline and/or placebo) may be measured from one time point to another. Some clinically relevant time courses include 0-12 hr, 0-24 hr, 12-24 hr after dose administration. In the context of 24 hour efficacy for QD dosing, the $FEV_1AUC(12\text{-}24\text{ hr})$ (baseline- and/or placebo-adjusted $FEV_1$ area under the curve (AUC) from 12 to 24 hours after administration of the muscarinic antagonist to the patient) is particularly relevant. In some embodiments, an $FEV_1AUC(12\text{-}24\text{ hr})$ of at least 0.5 L·hr for inhaled glycopyrrolate is required to achieve prolonged duration of bronchodilation over 24 hours. In some embodiments, an $FEV_1AUC(12\text{-}24\text{ hr})$ of greater than 40% of the $FEV_1AUC(0\text{-}12\text{ hr})$ for inhaled glycopyrrolate is required to achieve prolonged duration of bronchodilation over 24 hours.

Mean $FEV_1$: This is the mean $FEV_1$ between two time points, calculated by dividing the $FEV_1AUC_{t1\text{-}t2}$ (wherein $t_1$ is the starting time and $t_2$ is the ending time for the relevant time course) by the difference between $t_2$ and $t_1$. Some clinically relevant time courses for Mean $FEV_1$ include 0-12 hr, 0-24 hr, 12-24 hr, after dose administration. In the context of 24 hour efficacy for QD dosing, the Mean $FEV_1$ (12-24) (placebo-adjusted Mean $FEV_1$ from 12 to 24 hours after the muscarinic antagonist to the patient) is particularly relevant.

Trough $FEV_1$: This is the $FEV_1$ value measured just prior to administration of the drug (e.g. just prior to the next administration of the drug). In some cases, the trough $FEV_1$ is obtained in the morning, just prior to administration of the drug. In some embodiments, the change in trough $FEV_1$ is the difference between the trough $FEV_1$ for the drug and the trough $FEV_1$ for a placebo, after a period of time. In general, for a once daily (QD) bronchodilator drug, trough $FEV_1$ (at 24 hours post-dosing and, prior to administration of the next dose) is considered the clinically relevant endpoint. In some embodiments, the change in the trough. $FEV_1$ is measured over a predetermined time course, such as 1 wk, 2 wk, 4 wk or 12 wk.

FVC: Forced Vital Capacity, which is the maximal volume of air exhaled with maximal effort from a position of maximal inhalation. It is expressed in liters and in percentage of a patient's reference value from baseline, $FEV_1/FVC$: The quotient of $FEV_1$ and PVC.

PEF: Peak Expiratory Flow, which is the highest expiratory flow achieved with maximal effort from a position of maximal inspiration. This is essentially the speed of the air moving out of the lungs of a patient at the beginning of expiration. It is expressed in liters/second or in liters/minute.

$PEF_{25\text{-}75}$: Forced Expiratory Flow from 25% to 75% on the flow-volume curve, which is the average flow (or speed) of air coming out of the lung during the middle portion of expiration.

$FEF_{25\text{-}50}$: Forced Expiratory Flow from 25% to 50% on the flow-volume curve, which is another measure of the average flow (or speed) of air coming out of the lung during the initial portion of expiration.

$FIF_{25\text{-}75}$: Forced Inspiratory Flow from 25% to 75% on the flow-volume curve, which is the average flow (or speed) of air entering the lung during the middle portion of inspiration.

$FIF_{25\text{-}50}$: Forced Inspiratory Flow from 25% to 50% on the flow-volume curve, which is another measure of the average flow (or speed) of air entering the lung during the initial portion of inspiration.

An enhanced therapeutic effect can include an increased magnitude of therapeutic effect, an enhanced duration of therapeutic effect, an enhanced time to onset of therapeutic effect, a shorter time to maximum therapeutic effect or a greater magnitude of therapeutic effect. In some embodiments described herein, an enhanced therapeutic effect relates to the increased ability of a pharmaceutical agent to relieve the symptoms of an airway respiratory disorder, e.g. COPD, Thus, an enhanced therapeutic effect may be determined by comparing values of change in $FEV_1$ (i.e. change in $FEV_1$ from baseline or compared to a placebo). % change in $FEV_1$ (i.e. percent change in $FEV_1$ from baseline or compared to placebo), $FEV_1$ AUC, trough $FEV_1$, $FEV_1$/FVC, PEF, $FEF_{25\text{-}75}$, $FEF_{25\text{-}50}$, $FIF_{25\text{-}75}$, $FIF_{25\text{-}50}$ obtained from a patient or patient population in one therapeutic milieu versus another anther therapeutic milieu. For example, an enhanced therapeutic effect may be determined by comparing $FEV_1$ values for a patient or patient population treated with a muscarinic antagonist administered with a high efficiency nebulizer against the same drug administered with a conventional nebulizer. In another example, an enhanced therapeutic effect may be determined by comparing $FEV_1$ values for a patient or patient population treated with a muscarinic antagonist administered at a high concentration against the same drug administered at a low concentration. In some cases, an enhanced therapeutic effect may be determined by comparing $FEV_1$ values for a patient or patient population treated with a muscarinic antagonist administered with a high efficiency nebulizer against a muscarinic antagonist alone administered with a conventional nebulizer. In another example, an enhanced therapeutic effect may be determined by comparing $FEV_1$ values for a patient or patient population treated with a muscarinic antagonist administered at a high concentration against a muscarinic antagonist alone administered at a low concentration. In some embodiments, the enhanced therapeutic effect is an increased magnitude of therapeutic effect. In some embodiments, the increased magnitude of therapeutic effect is an increase in the peak $FEV_1$ obtained with a high efficiency nebulizer versus the peak $FEV_1$ obtained with a conventional nebulizer. In some embodiments, the peak $FEV_1$ obtained with a high efficiency nebulizer is at least about 10%, 15%, 20%, or 30% above that obtained with a conventional nebulizer. In some embodiments, the peak $FEV_1$ obtained with a high efficiency nebulizer is at least about 25 mL, 50 mL, or 100 mL above that obtained with a conventional nebulizer. In some embodiments, the increased magnitude of therapeutic effect is an increase in the mean $FEV_1$ obtained with a high efficiency nebulizer versus the mean $FEV_1$ obtained with a conventional nebulizer. In some embodiments, the mean $FEV_1$ obtained with a high efficiency nebulizer is at least about 5%, 10%, or 15% above that obtained with a conventional nebulizer. In some embodiments, the mean $FEV_1$ obtained with a high efficiency nebulizer is at least about 50 mL, 100 mL, or 150 mL above that obtained with a conventional nebulizer. In some embodiments, the increased magnitude of therapeutic effect is an increase in the AUC for the $FEV_1$ versus time curve obtained with a high efficiency nebulizer versus the AUC for the $FEV_1$ versus time curve obtained with a conventional nebulizer. In some embodiments, the increase in AUC of the $FEV_1$ versus time curve obtained with a high efficiency nebulizer is at least about 50%, 75% or 100% above that obtained with a conventional nebulizer.

In some embodiments, the method or system (e.g. muscarinic antagonist, optionally in combination with a beta 2-adrenergic agonist, administered at a high concentration and/or with a high efficiency nebulizer) provides an enhanced duration of therapeutic effect, as determined by the amount of time that a spirometric parameter (e.g. $FEV_1$, trough $FEV_1$) is above a predetermined threshold after therapy is administered. In some embodiments, the predetermined threshold is at least about 5% above baseline, at least about 10% above baseline, at least about 15% above baseline, at least about 20% above baseline, at least about 25% above baseline. In some specific embodiments, the threshold is about 15% above baseline. In some specific embodiments, the threshold is about 10% above baseline. In some embodiments, the threshold is 50 mL, 100 mL, 150 mL or more than about 150 mL above baseline. In some specific embodiments, the threshold is about 100 mL above baseline. Baseline can be determined by either a one-time reference to the spirometric parameter (e.g. $FEV_1$) immediately prior to administration of API, or by reference to the spirometric parameter level at several time periods during the study following administration of placebo to a predetermined set of patients. In some embodiments, baseline is determined based on the level of spirometric parameter (e.g. $FEV_1$) immediately prior to administration to the patient of muscarinic antagonist administered at a high concentration and/or with a high efficiency nebulizer. In some embodiments, baseline is determined by reference to the level of spirometric parameter (e.g. $FEV_1$) at several time periods (e.g., 12 hours, 24 hours) during evaluation of certain patients following placebo administration, with the simultaneous evaluation of other patients administered a muscarinic antagonist administered at a high concentration and/or with a high efficiency nebulizer.

In some embodiments, a duration of therapeutic effect is the period during which $FEV_1$ is at least about 5% above baseline, at least about 10% above baseline, at least about 15% above baseline, at least about 20% above baseline, at least about 25% above baseline. In some specific embodiments, the duration of therapeutic effect is the amount of time that the $FEV_1$ is at least 15% above baseline. In some specific embodiments, the duration of therapeutic effect is the amount of time that the FEN) is at least 10% above baseline. In some specific embodiments, the duration of therapeutic effect is the amount of time that the $FEV_1$ is at least 50 mL, 100 mL, or 150 mL above baseline. In some embodiments, a duration of therapeutic effect is the period during which $FEV_1/FVC$ is at least about 5% above baseline, at least about 10% above baseline, at least about 15% above baseline, at least about 20% above baseline, at least about 25% above baseline. In some embodiments, the duration of therapeutic effect is the amount of time that the $FEV_1/FVC$ is at least 15% above baseline. In some embodiments, a duration of therapeutic effect is the period during which PEF is at least about 5% above baseline, at least about 10% above baseline, at least about 15% above baseline, at least about 20% above baseline, at least about 25% above baseline. In some embodiments, the duration of therapeutic effect is the amount of time that the PEF is at least 15% above baseline. In some embodiments, a duration of therapeutic effect is the period during which $FEF_{25-75}$ is at least about 5% above baseline, at least about 10% above baseline, at least about 15% above baseline, at least about 20% above baseline, at least about 25% above baseline. In some embodiments, the duration of therapeutic effect is the amount of time that the $FEF_{25-75}$ is at least 15% above baseline. In some embodiments, a duration of therapeutic effect is the period during which $FEF_{25-50}$ is at least about 5% above baseline, at least about 10% above baseline, at least about 15% above baseline, at least about 20% above baseline, at least about 25% above baseline. In some embodiments, the duration of therapeutic effect is the amount of time that the $FEF_{25-50}$ is at least 15% above baseline. In some embodiments, a duration of therapeutic effect is the period during which $FIF_{25-75}$ is at least about 5% above baseline, at least about 10% above baseline, at least about 15% above baseline, at least about 20% above baseline, at least about 25% above baseline. In some embodiments, the duration of therapeutic effect is the amount of time that the $FIF_{25-75}$ is at least 15% above baseline. In some embodiments, a duration of therapeutic effect is the period during which $FIF_{25-50}$ is at least about 5% above baseline, at least about 10% above baseline, at least about 15% above baseline, at least about 20% above baseline, at least about 25% above baseline. In some embodiments, the duration of therapeutic effect is the amount of time that the $FIF_{25-50}$ is at least 15% above baseline.

A significantly greater, or greater, duration of therapeutic effect, indicates that the method or system (e.g. a high efficiency nebulizer-administered muscarinic antagonist) provides an increased period of time the spirometric parameter is above a predetermined threshold of about 5% above baseline, about 10% above baseline, about 15% above baseline, about 20% above baseline, about 25% above baseline, especially about 15% above baseline, for one or more of the spirometric parameters compared to the same spirometric parameter obtained with substantially the same nominal dose of drug administered with a different inhalation device, e.g. a conventional nebulizer. In some embodiments, the threshold for the spirometric parameter (e.g. $FEV_1$, or trough $FEV_1$) is 50 mL, 100 mL, 150 mL or more than about 150 mL above baseline. In some specific embodiments, the threshold is about 100 mL above baseline.

"About the same" duration of therapeutic effect means that the method or system (e.g. a high efficiency nebulizer-administered muscarinic antagonist, optionally in combination with a beta 2-adrenergic agonist) provides substantially the same period of time that the spirometric parameter is above a predetermined threshold of about 5% above baseline, about 10% above baseline, about 15% above baseline, about 20% above baseline, about 25% above baseline, or especially about 15% above baseline, for one or more of the above spirometric parameters compared to the same spirometric parameter obtained with a substantially greater nominal dose of the muscarinic antagonist administered with a different inhalation device, e.g. conventional nebulizer (reference administration).

In some embodiments, an inhalation solution described herein (e.g. a muscarinic antagonist inhalation solution administered with a high efficiency nebulizer and/or at a high concentration) provides a duration of therapeutic effect of at least about 12 hr, about 12 hr to about 24 hr, about 18 hr to about 24 hr. about 20 hr to about 24 hr, or at least about 24 hr, in some embodiments.

A time to onset of therapeutic effect is the time for the spirometric parameter to reach a predetermined threshold of about 5% above baseline, about 10% above baseline, about 15% above baseline, about 20% above baseline, or about 25% above baseline, especially about 15% above baseline for one or more of the spirometric parameters of a muscarinic antagonist administered with an inhalation device. An enhanced time to onset of therapeutic effect relates to the increased ability of a pharmaceutical agent to relieve the symptoms of an airway respiratory disorder, e.g. COM. The enhanced time to onset of therapeutic effect may be a measure of the $FEV_1$, $FEV_1/FVC$, PEF, $FEF_{25-75}$, $FEF_{25-50}$, $FIF_{25-75}$, $FIF_{25-50}$ levels.

A significantly shorter, or shorter, time to onset of therapeutic effect, in some embodiments, means that the method or system (a muscarinic antagonist inhalation solution administered with a high efficiency nebulizer and/or at a high concentration) provides for a shortened period of time for one or more spirometric parameters (e.g., $FEV_1$) to reach a predetermined threshold of about 5% above baseline, about 10% above baseline, about 15% above baseline, about 20% above baseline, or about 25% above baseline, especially about 15% above baseline, for one or more of the spirometric parameters compared to the same spirometric parameter(s) obtained with substantially the same nominal dose of the drug solution administered with a different inhalation device, e.g. a conventional nebulizer and/or at a lower concentration. In other embodiments, "about the same" time to onset of therapeutic effect means the method or system (e.g. administration of a muscarinic antagonist with a high efficiency nebulizer and/or at a high concentration) provides for substantially the same period of time for the spirometric parameter to reach a predetermined threshold of about 5% above baseline, about 10% above baseline, about 15% above baseline, or about 20% above baseline for one or more of the spirometric parameters compared to the same spirometric parameter obtained with a substantially greater nominal of the dose the drug solution administered with a different inhalation device, e.g. a conventional nebulizer.

An inhalation solution that provides an onset of therapeutic effect of less than about 30 minutes, less than about 25 minutes, less than about 20 minutes, less than about 15 minutes, or less than about 10 minutes, in some embodiments, refers to an amount of time for the spirometric parameter to reach a predetermined threshold of about 5% above baseline, about 10% above baseline, about 15% above baseline, or about 20% above baseline.

In some embodiments, the methods or systems are provided for the treatment of acute exacerbations of chronic obstructive pulmonary disease (AECOPD), chronic bronchitis, and/or emphysema in a patient, comprising administering to the patient a nominal dose of a muscarinic antagonist, optionally in combination with a long-acting or short-acting beta 2 agonist, with a high efficiency nebulizer to provide a rapid onset of therapeutic effect and a long duration of therapeutic effect. In some embodiments, the rapid onset of therapeutic effect is less than about 30 minutes, less than about 25 minutes, less than about 20 minutes, less than about 15 minutes or less than about 10 minutes. In some embodiments, the long duration of therapeutic effect is at least about 12 hr to about 24 hr, about 18 hr to about 24 hr, about 20 hr to about 24 hr or at least about 24 hr.

A time to maximum therapeutic effect means the amount of time for a preselected spirometric parameter to reach its peak level. In some embodiments, an enhanced time to maximum therapeutic effect means that administration of a muscarinic antagonist with a high efficiency nebulizer, at a high concentration or both, results in a faster time to maximum therapeutic effect than would a dose of the muscarinic antagonist administered with a conventional nebulizer or at a lower concentration. The parameters used to determine an enhanced time to maximum therapeutic effect may be one or more of $FEV_1$, $FEV_1$/FVC, PEF, $FEF_{25-75}$, $FEF_{25-50}$, $FIF_{25-75}$, or $FIF_{25-50}$.

Reduction in Adverse Side Effects

Conventional COPD therapy employing a muscarinic antagonist with a conventional nebulizer often results in deposition of pharmaceutically active ingredient in sections distinct from the lung, e.g., mouth, throat, stomach, and/or esophagus. This results in antagonism of muscarinic receptors on peripheral systems other than the lung, for example in salivary glands, stomach, heart, and/or CNS and elsewhere. Therefore the tolerated doses of systemically active muscarinic antagonists, such as glycopyrrolate, are limited by side-effects such as, but not limited to, xerostomia (dry mouth), urinary hesitancy and retention, blurred vision, tachycardia, dizziness, insomnia, impotence, mental confusion, excitement, headache, anxiety, hypotension and/or palpitations.

In the present invention, the bronchodilation and other beneficial actions of a muscarinic antagonist are produced by an inhaled agent providing for a high therapeutic index for activity in the lung, i.e. lung deposition, compared with deposition of muscarinic antagonist in non-pulmonary regions, i.e. periphery compartments, mouth and pharynx. The present invention further provides for an inhalable muscarinic antagonist with low bioavailability in areas within a patient other than the lung (e.g. systemic bioavailability, local oropharyngeal or gastric regions), resulting in a decreased incidence and/or severity of systemic and/or local toxicity and/or side effects. A practitioner of ordinary skill can quantify a reduction in adverse side effects by measuring the incidence and/or severity of systemic and/or local toxicity and/or side effects in a given patient or patient population.

A reduced, or decreased, incidence or severity of systemic and/or local toxicity and/or side effects means that the method or system (e.g. muscarinic antagonist, optionally in combination with a beta 2-adrenoceptor agonist, administered with a high efficiency nebulizer and/or at a high concentration) provides a decreased incidence and/or severity of systemic and/or local toxicity and/or side effects (for example dry mouth) in a given patient or patient population compared to a given reference therapy. In some embodiments, the reference therapy is administration of a muscarinic antagonist with a conventional nebulizer. Some embodiments provide a method for the treatment of COPD in a patient, comprising administering to the patient a nominal dose of muscarinic antagonist which, when administered with a high efficiency nebulizer, provides a calculated respirable dose of a muscarinic antagonist with a high efficiency nebulizer, wherein the calculated respirable dose of the muscarinic antagonist administered with the high efficiency nebulizer demonstrates a decreased incidence and/or severity of systemic and/or local toxicity and/or side effects in the patient as compared to a nominal dose that achieves substantially the same calculated respirable dose of the muscarinic antagonist administered with a conventional nebulizer. Some embodiments provide a method for the treatment of COPD in a patient, comprising administering to the patient a nominal dose of muscarinic antagonist which, when administered with a high efficiency nebulizer, provides a deposited lung dose of a muscarinic antagonist with a high efficiency nebulizer, wherein the deposited lung dose of the muscarinic antagonist administered with the high efficiency nebulizer demonstrates a decreased incidence and/or severity of systemic and/or local toxicity and/or side effects in the patient as compared to a nominal dose that achieves substantially the same deposited lung dose of the muscarinic antagonist administered with a conventional nebulizer. Some embodiments provide a system for performing the foregoing methods.

In some embodiments, the method or system (e.g. administration of a muscarinic antagonist with a high efficiency nebulizer and/or at a high concentration) provides a method and/or inhalation system for administration of a muscarinic antagonist in a volume of about 0.5 mL or less, 1 mL or less, 1.5 mL or less, or 2.0 mL or less and wherein the muscarinic antagonist demonstrates less incidence and/or severity of systemic and/or local toxicity and/or side effects (for example dry mouth) in the patient as compared to substantially the same nominal dose of the muscarinic antagonist administered in a substantially higher volume of solution.

In some embodiments, the method or system (e.g. muscarinic antagonist with a high efficiency nebulizer and/or at a high concentration) provides for methods and inhalation systems for reducing at least one side effect of the muscarinic antagonist and providing a duration of therapeutic effect of at least about 12 hr, about 12 hr to about 24 hr, about 18 hr to about 24 hr, about 20 hr to about 24 hr, or at least about 24 hours. In some embodiments, the method or system (e.g. administration of a muscarinic antagonist with a high efficiency nebulizer and/or at a high concentration) provides for co-administration of other drugs and optionally excipients, for example an organic acid, such as ascorbic acid, citric acid or a mixture of both, pilocarpine, cevimeline or carboxymethylcellulose, or a mucolytic compound.

Enhanced Lung Deposition

Muscarinic receptors and beta 2-adrenoceptors are widely distributed throughout the body. The ability to apply these active pharmaceutical agents (APIs) locally to the respiratory tract with sufficient lung deposition is particularly advantageous, as it would allow for administration of lower doses of the drug fostering increased patient compliance The principle advantage of administration of a nebulized API solution with a high efficiency nebulizer over other methods of pulmonary delivery of APIs is that the methods and systems described herein offer more efficient delivery of higher doses of API compared to conventional inhalation methods and systems, resulting in greater efficacy and a reduced incidence and optionally a severity of side effects in the patient. A more efficient delivery of API is evidenced by direct delivery and deposition of an API to the site of action, i.e. the lung (as used herein, "lung" refers to either or both the right and left lung organs). It can be assumed that substantially all of an API delivered at the receptor site in the lungs will be absorbed into the blood plasma of the patient. In embodiments of the invention, the API is a muscarinic antagonist (optionally in combination with a beta 2-adrenoceptor agonist), such as glycopyrronium bromide (glycopyrrolate).

The deposited dose may be expressed in terms of lung deposition. A lung deposition of 30% means 30% of the active ingredient in the inhalation device just prior to administration is deposited in the lung. Likewise, a lung deposition of 60% means 60% of the active ingredient in the inhalation device just prior to administration is deposited in the lung, and so forth. Lung deposition (deposited lung dose) can be determined using methods of scintigraphy or deconvolution. In some embodiments, the present invention provides for methods and inhalation systems for the treatment or prophylaxis of a respiratory condition in a patient, comprising administering to the patient a nominal dose of a muscarinic antagonist solution with a high efficiency nebulizer wherein administration of the muscarinic antagonist with the inhalation device provides lung deposition (deposited lung dose) of the muscarinic antagonist of at least about 30%, at least about 35%, at least about 40%, at least about 45%, at least about 50%, at least about 55%, at least about 60%, about 30% to about 60%, about 30% to about 55%, about 30% to about 50%, about 30% to about 40%, about 30% to about 90%, about 40% to about 80%, about 50% to about 60%, or about 60% to about 70% based on the nominal dose of the muscarinic antagonist. In some embodiments, the present invention provides for methods and inhalation systems for the treatment or prophylaxis of a respiratory condition in a patient, comprising administering to the patient a nominal dose of a muscarinic antagonist in an aqueous inhalation solution with an inhalation device wherein administration of the muscarinic antagonist with the inhalation device provides lung deposition (deposited lung dose) of the muscarinic antagonist of at least about 15%, at least about 20%, at least about 25%, at least about 30%, at least about 35%, at least about 40%, at least about 45%, at least about 50%, at least about 55%, at least about 60%, about 20% to about 40%, about 25% to about 35%, about 25% to about 30%, about 35% to about 90%, about 40% to about 80%, about 50% to about 60%, or about 60% to about 70% based on the nominal dose of the muscarinic antagonist.

Aerosol particle/droplet size is one of the most important factors determining the deposition of aerosol drugs in the airways. The portion of an aerosol that has the highest probability of bypassing the upper airway and depositing in the lung measure between 1 and 5 µm. Particles larger than this are generally deposited in the oropharyngeal region and are swallowed, while sub-micron particles do not carry much drug and may be exhaled before deposition takes place or are absorbed systemically. Smaller particles tend to deposit more peripherally in the lung than coarser particles, which may lead to a different clinical response. Consequently, differences in particle size of the aerosol emitted from inhalation devices may account for some of the variability in therapeutic efficacy and safety. Measurement of particle size, therefore, has an important role in guiding product development and in quality control of the marketed product.

The distribution of aerosol particle/droplet size can be expressed in terms of either or both of:

The Mass Median Aerodynamic Diameter (MMAD) and the Geometric Standard Deviation (GSD), wherein the MMAD is the droplet size at which half of the mass of the aerosol is contained in smaller droplets and half in larger droplets and the GSD is the geometric standard deviation of the particle population. While MMAD is most often determined by a cascade impactor apparatus, the mass median diameter (MMD) is most often measured by laser diffraction and can be used as a surrogate for the MMAD value.

The Fine Particle Fraction (FPF), which is the fraction of particles (which may be expressed as a percentage) that are <5 µm in diameter.

These measures have been used for comparisons of the in vitro performance of different inhaler device and drug combinations. In general, the higher the fine particle fraction; the higher the proportion of the emitted dose that is likely to reach the lung.

There are two main methods used to measure aerosol deposition in the lungs. First, γ-scintigraphy is performed by radiolabeling the drug with a substance like 99 m-technetium, and scanning the subject after inhalation of the drug. This technique has the advantage of being able to quantify the proportion of aerosol inhaled by the patient, as well as regional distribution in the upper airway and lungs. Second, since most of the drug deposited in the lower airways will be absorbed into the bloodstream, pharmacokinetic techniques are used to measure lung deposition (deposited lung dose). This technique can assess the total amount of drug that interacts with the airway epithelium and is absorbed systemically, but will miss the small portion that may be expectorated or swallowed after mucociliary clearance, and cannot tell us about regional distribution. Therefore, γ-scintigraphy and pharmacokinetic studies are in many cases considered complementary.

The relationship between pulmonary deposition of inhaled β2-agonists and therapeutic effect is now well-established, since the immediate effects of these agents on the airways are relatively easy to measure. As the pulmonary dose response curve for the β2-agonists is sigmoidal (i.e. an initial slope followed by a plateau), increasing the dose deposited in the lung will elicit an increased therapeutic effect only if the initial dose was on the rising slope of the dose response curve.

Lung deposition of a particular drug is influenced by the mass of drug contained in the nebulized droplets administered to a patient with a particular Mass Median Aerodynamic Diameter (MMAD) and Geometric Standard Deviation (GSD). In general, there is an inverse relationship between the average MMAD and GSD of a particular nebulizer's emitted droplets and deposition of the droplets in a patient's lung. A smaller MMAD results in an increased likelihood of lung deposition in a patient. When the MMAD is in the range of about 3.0-4.5 µm, a narrower GSD results in a higher degree of lung deposition, since a higher percentage of particles will be under 5 µm in diameter. It is believed that, in general, aerosol particles greater than 10 µm in aerodynamic diameter deposit primarily in the oropharynx and are swallowed rather than reaching the lungs. Because of the plausible link between MMAD and GSD values and eventual deposition site within the respiratory tract, smaller MMAD and GSD values may affect both the safety (by reducing non-pulmonary deposition and possibly thereby, reducing local and potentially systemic effects) and the efficacy (by increasing the amount of drug actually deposited in the lungs) of drug products administered with such high efficiency inhalation devices. Cascade impaction and laser-diffraction provides for an in vitro method of determining MMAD (or MMD) and GSD data, which can then be plotted onto what usually results in a log-normal shaped curve (depicting mass distribution % on the Y-axis and droplet diameter on the X-axis). Laser-diffraction methods are well-known to one of ordinary skill in the art. In addition to laser-diffraction methods, in vitro data for MMAD and GSD can also be measured using cascade impaction or time-of-flight analytical methods, both of which are known to one of ordinary skill in the art.

Geometric Standard Deviation (GSD) is a dimensionless measure of dispersion from a geometric mean, such as the MMAD. In general, the smaller the GSD for a particular particle size distribution, the narrower the distribution curve. In some embodiments, administration of the muscarinic antagonist with the high efficiency nebulizer provides a GSD of emitted droplet size distribution of the solution administered with a high efficiency nebulizer of about 1.1 to about 2.1, about 1.2 to about 2.0, about 1.3 to about 1.9, less than about 2, at least about 1.4 to about 1.8, at least about 1.5 to about 1.7, about 1.4, about 1.5, or about 1.6. In some embodiments, administration of API with a high efficiency nebulizer provides a Mass Median Aerodynamic Diameter (MMAD) of droplet size of the solution emitted with the high efficiency nebulizer of about 1 µm to about 5 µm, about 2 to about 4 µm, about 3 to about 4 µm, or about 3.5 to about 4.5 µm.

Respirable Fraction (RE), Emitted Dose (ED) or Delivered Dose (DD), Respirable Dose (RD), and the Respirable Dose Delivery Rate (RDDR) are in vitro-derived (calculated) parameters that provide technical dimensions for the efficiency of a nebulizer inhalation device. RF, which is measured with a cascade impactor or laser diffraction apparatus, is a generally accepted estimate within the medical community of the fraction, which may be expressed as a percentage, of drug that is available for lung deposition. Droplets of less than 5.0 µm in diameter are considered to penetrate to the lung and can be defined as "RF<5 µm" (i.e. fine particle fraction (FPF)). In some embodiments, administration of the muscarinic antagonist with a high efficiency nebulizer provides a respirable fraction (RE) of API of at least about 60%, at least about 65%, at least about 70%, at least about 75%, at least about 80%, at least about 85%, at least about 90%, about 60% to about 95%, about 65% to about 95%, or about 70% to about 90%. In some embodiments, the high efficiency nebulizer is characterized by an RF of at least about 80% or about 70% to about 90%.

The Emitted Dose (ED), or Delivered Dose (DD), of drug administered to a patient is the portion of volume of liquid filled into the nebulizer, i.e. the fill volume, which is actually emitted from the mouthpiece of the device. The difference between the nominal dose and the ED is the amount of volume lost primarily to residues, i.e. the amount of fill volume remaining in the nebulizer after administration, or is lost in aerosol form. The ED of the muscarinic antagonist is to be tested under simulated breathing conditions using a standardized bench setup, which are known to one of skill in the art. In some embodiments, the ED of the muscarinic antagonist of the present invention is at least about 30%, at least about 35%, at least about 40%, at least about 45%, at least about 50%, at least about 55%, at least about 60%, about 30% to about 60%, about 30% to about 55%, about 30% to about 50%, about 30% to about 40%, about 30% to about 75%, about 40% to about 70%, or about 45% to about 60%. The Respirable Dose (RD) is an expression of the delivered mass of drug contained within emitted droplets from a nebulizer that are small enough to reach the lung of a patient. The RD is determined by multiplying the ED by the RF, and can be readily determined using the respective ED and RE values provided herein.

The output rate is the speed at which API is administered from the inhalation device. In some embodiments, administration of the muscarinic antagonist with the high efficiency nebulizer provides an output rate of API of at least about 2 times, 3 times or 4 times the output rate achievable with a conventional nebulizer. For example, where the muscarinic antagonist is glycopyrrolate, in some embodiments the output rate is at least about 120 µg/min, at least about 150 µg/min, at least about 200 µg/min or at least about 200 µg/min to at least about 5,000 µg/min. In some embodiments, administration of glycopyrrolate with the high efficiency nebulizer provides an output rate of API of at least about 120 µL/min, at least about 150 µL/min, at least about 200 µL/min or at least about 200 µL/min to at least about 5,000 µL/min.

Figure 3:
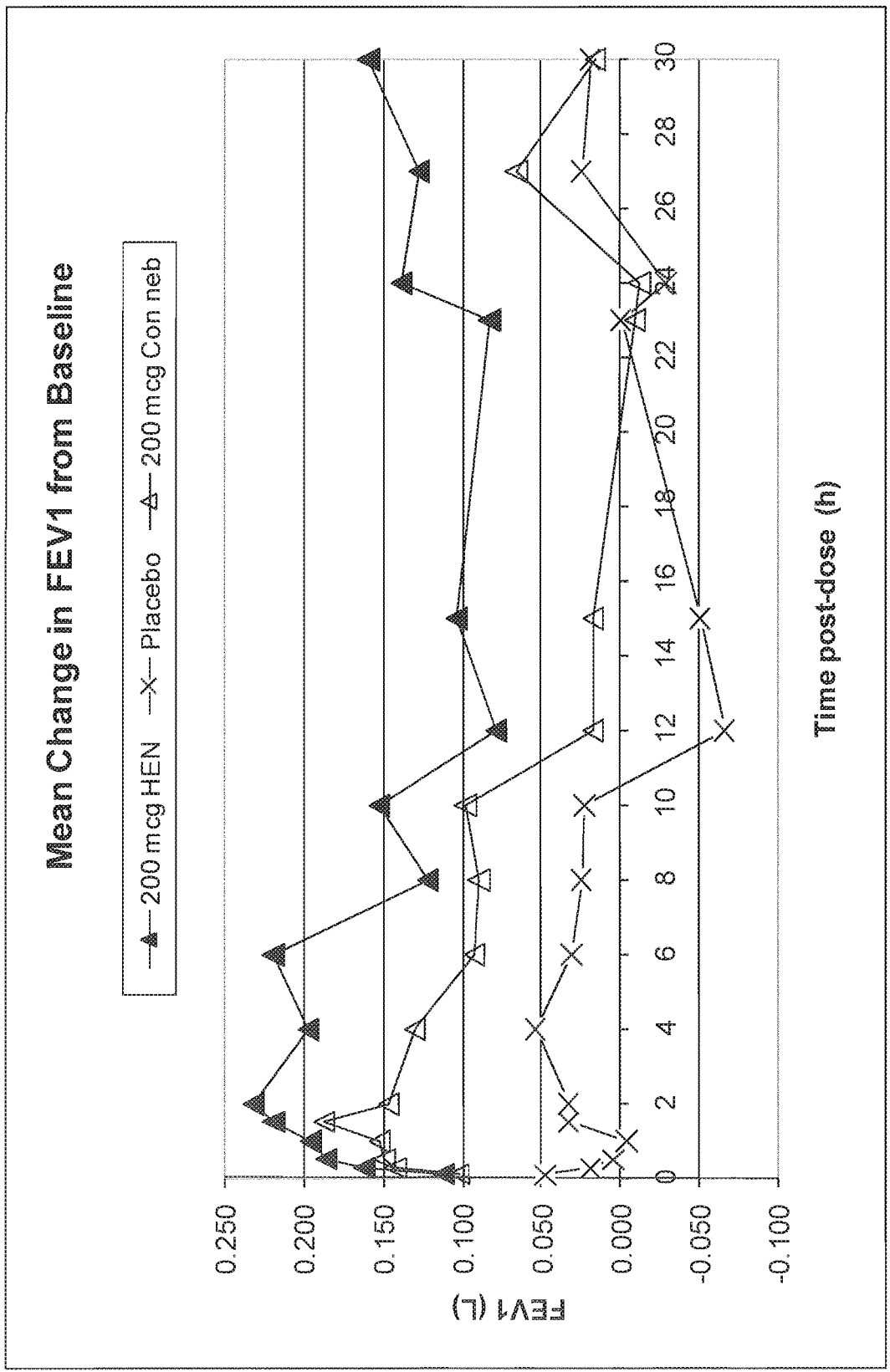
FIG. 3 is a graph comparing lung function response ($FEV_1$ (L) change from baseline) over a time course of 30 hours for 200 µg of glycopyrrolate administered with a high efficiency nebulizer, 200 µg of glycopyrrolate administered with a conventional jet nebulizer, and placebo (saline) administered with the conventional jet nebulizer. The glycopyrrolate dose administered with the high efficiency nebulizer provided a mean improvement in peak lung function (peak $FEV_1$) of about 45 mL compared to the same glycopyrrolate dose administered in the conventional jet nebulizer. Also, the glycopyrrolate dose administered with the high efficiency nebulizer provided improvement in lung function of greater than 100 mL $FEV_1$ above baseline at the 24 hour time point, whereas the same dose administered with the conventional jet nebulizer failed to achieve an increase in $FEV_1$ above baseline greater than 100 mL at any time point after 12 hr.

The Respirable Dose Delivery Rate (RDDR) is the speed at which a respirable dose of the drug is nebulized, administered, and delivered to a patient's lungs. RDDR, measured as a function of μg/min, is determined by dividing the RD (in μg) by the amount of time necessary for inhalation. The amount of time necessary for inhalation is measured as the amount of time from the first moment of administration of the emitted droplet from the nebulizer until the emitted droplet of respirable diameter is delivered to the lung, as measured using a standardized bench setup simulating breathing conditions. In some embodiments, administration of the muscarinic, antagonist to the patient with the high efficiency nebulizer provides a respirable dose delivery rate (RDDR) of at least about 2 times, 3 times or 4 times the delivery rate achievable with a conventional nebulizer. Where the muscarinic antagonist is glycopyrrolate, in some embodiments the RDDR is at least about 100 μg/min, at least about 150 μg/min, at least about 200 μg/min, about 100 μg/min to about 5,000 μg/min, about 150 μg/min to about 4,000 μg/min or about 200 μg/min to about 3,500 μg/min. In some embodiments, administration of the glycopyrrolate to the patient with an aqueous inhalation device provides an RDDR of at least about 100 μg/min or about 100 μg/min to about 5,000 μg/min.

EXAMPLES

The following ingredients, processes and procedures for practicing the systems and methods disclosed herein correspond to that described above. The procedures below describe some embodiments of methods of delivery of a nebulized long-acting cholinergic antagonist aqueous solution (as a mono therapeutic agent), or in combination with a nebulized β2-adrenoceptor aqueous solution (in combination therapy) as described herein and pharmacokinetic profiles thereof. Methods, materials, or excipients which are not specifically described in the following examples are within the scope of the invention and will be apparent to those skilled in the art with reference to the disclosure herein.

Example 1: Single-Dose, Dose Escalation Study to Assess Glycopyrrolate Inhalation Solution (GIS) Using a High Efficiency Nebulizer in Patients with COPD Objectives:

The objectives of the study were as follows: Primary: To assess the safety and tolerability of single ascending doses of glycopyrrolate inhalation solution when administered using a high efficiency nebulizer in patients with COPD. Secondary: (1) To assess and to compare the magnitude and duration of bronchodilator response in patients with COPD following single doses of glycopyrrolate inhalation solution when administered using a high efficiency nebulizer and a conventional jet nebulizer; and (2) To assess the pharmacokinetic (PK) profile of an inhaled glycopyrrolate solution formulation.

Methodology:

This two part study was a two-center, single dose, dose-escalation study in patients with COPD of 40-75 years of age. There were 12 subjects included in the study.

Part 1 was an open label study to assess the safety, tolerability, PK profile and bronchodilator response following single doses of glycopyrrolate inhalation solution when administered via a high efficiency nebulizer. Subjects were studied in two cohorts in parallel. Prior to treatment, subjects received a thorough medical examination (Screening Visit). A Treatment Period consisted of two doses of glycopyrrolate inhalation solution being administered in the first cohort in a dose-escalation manner at two separate visits (Treatment Visits), and three doses being administered in the second cohort in three separate visits (Treatment Visits), with a washout period of 5 to 12 days between doses for both cohorts. After identifying an effective dose of glycopyrrolate inhalation solution that provided 24 hours of bronchodilation when using a high efficiency nebulizer in Part 1, all subjects entered Part 2 of the study and received, in a randomized, double-blind manner, a single dose of either glycopyrrolate inhalation solution (as determined in Part 1) or placebo via a conventional jet nebulizer. The high efficiency nebulizer tested was the eFlow (PARI, Germany). The conventional jet nebulizer tested was a DeVilbiss 800 D.

Study procedures during each Treatment Period included serial spirometry (including $FEV_1$, FVC and PEFR) predose and immediately following dosing (within 5 minutes) and 15, 30 60, 90 minutes and 2, 4, 6, 8, 10, 12, 15, 23, 24, 27, and 30 hours post-dose. Blood samples were obtained to determine plasma GP concentrations at pre-dose and 5, 15, 30, 45 minutes and 1, 2, 4, 6, 8 and 12 hours post-dose. Vital signs and 12-lead electrocardiogram were obtained at predose and 30 and 60 minutes and 2, 4, 8, 12, 24 and 30 hours post-dose. Clinical labs were done at the Screening Visit and within 7 days following the last study treatment (Safety Follow-up Visit).

Study Treatments, Dose and Mode of Administration:

Part 1 (n=12): Subjects were randomly allocated to one of 2 cohorts running in parallel.

Cohort 1 (n=6): 1. Glycopyrrolate inhalation solution (GIS) 25 μg/0.5 mL oral inhalation via eFlow; 2. GIS 200 μg/0.5 mL oral inhalation via eFlow.

Cohort 2 (n:=6): 1. GIS 75 μg/0.5 mL oral inhalation via eFlow; 2. GIS 500 μg/0.5 mL oral; 3. GIS 1000 n/0.5 mL oral inhalation via eFlow.

Part 2 (n=12): All subjects who participated in Part 1 were included. Glycopyrrolate inhalation solution (200 mcg (μg) dose (selected from Part 1) or placebo in 2 mL solution formulation via the conventional jet nebulizer.

Assessments

The primary efficacy variable was serial spirometry throughout the 36 hour period after dosing. The spirometry assessments include forced expiratory volume in one second ($FEV_1$), forced vital capacity (FVC), peak expiratory flow rate (PEFR), $FEV_1$% of predicted normal.

The PK parameters to be evaluated for plasma glycopyrrolate are maximum concentration ($C_{max}$), time to maximum concentration ($T_{max}$), terminal elimination half-life ($T_{1/2}$), area under the plasma concentration-time curve from time=0 to time of last measurable drug concentration ($AUC_{0-t}$), and area under the plasma concentration-time curve from time=0 to infinity ($AUC_{0-inf}$).

Safety parameters include adverse events (AEs) including assessment of dry mouth, and changes in vital signs, 12-lead ECG (including QTc interval), and clinical laboratory tests.

The results are summarized in Table 1-1 and in FIG. 1 through FIG. 8.

In part 1, subjects in Cohort 1 received 25 μg and, after the washout period, 200 μg of glycopyrrolate with the high efficiency nebulizer, while Cohort 2 received 75 μg, 500 μg and 1000 μg doses of glycopyrrolate separated by washout periods. Based on the results of part 1, 200 μg of glycopyrrolate was chosen as the comparator for carrying into part 2 of the study.

In part 2, the two cohorts were randomized to a placebo group and an "active" group. The placebo group received normal saline and the "active" group received 200 μg of glycopyrrolate, both via the conventional jet nebulizer. The results of this study are depicted in the line graph in FIG. 3, where the 200 µg eFlow® high efficiency nebulizer results are also depicted for comparison. As can be seen in FIG. 3, the 200 µg dose of glycopyrrolate administered with the conventional jet nebulizer did not provide clinically meaningful improvement in $FEV_1$ at 12 hours and beyond, whereas the same dose administered with the high efficiency nebulizer provided clinically relevant improvements in $FEV_1$ up to and beyond the 24 hour time point. Also, the glycopyrrolate dose administered with the high efficiency nebulizer provided a mean improvement in peak lung function (peak $FEV_1$) of about 45 mL compared to the same glycopyrrolate dose administered in the conventional jet nebulizer.

Figure 4:
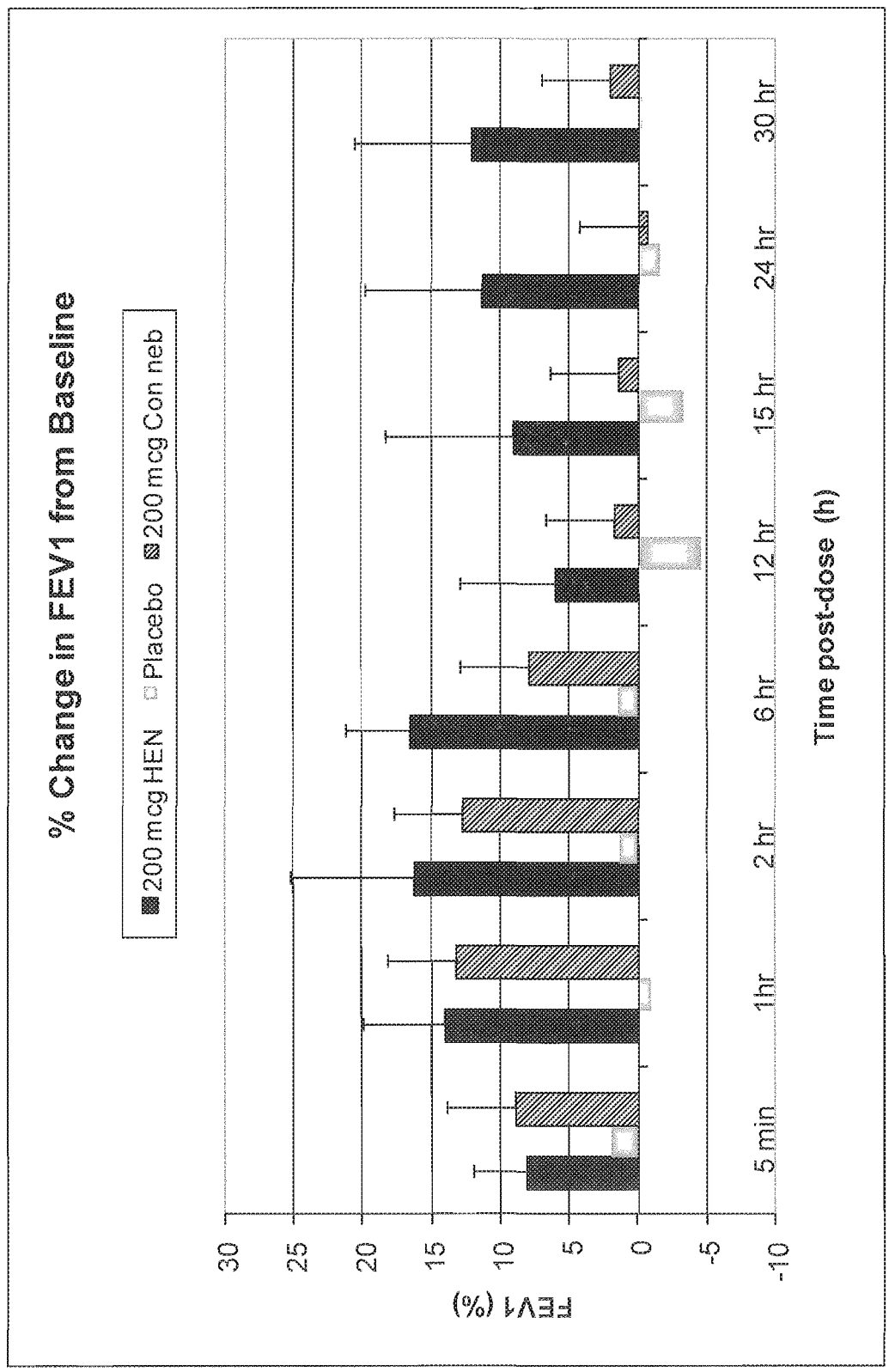
FIG. 4 is a graph comparing lung function response ($FEV_1$ (% change from baseline)) over a time course of 30 hours for 200 µg of glycopyrrolate administered with a high efficiency nebulizer (left-most bar at each time point), 200 µg of glycopyrrolate administered with a conventional jet nebulizer (right-most bar at each time point), and placebo (saline) administered with the conventional jet nebulizer (middle bar at each time point). The glycopyrrolate dose administered with the high efficiency nebulizer provided improvement in lung function of greater than 10% improvement in $FEV_1$ above baseline at the 24 hour time point, whereas the same dose administered with the conventional jet nebulizer failed to achieve an increase in $FEV_1$ above baseline greater than 10% at any time point after 12 hr.

FIG. 4 is a graph comparing lung function response (FEV1% change from baseline) over a time course of 30 hours for 200 µg of glycopyrrolate administered with a high efficiency nebulizer (left-most bar at each time point), 200 µg of glycopyrrolate administered with the conventional jet nebulizer (right-most bar at each time point), and placebo (saline) administered with the conventional jet nebulizer (middle bar at each time point). The glycopyrrolate dose administered with the high efficiency nebulizer provided improvement in lung function of greater than 10% in FEV1 above baseline at the 24 hour time point, whereas the same dose administered with the conventional jet nebulizer failed to achieve an increase in FEV1 above baseline greater than 10% at the 12 hr time point and beyond.

As shown in FIG. 1, which is a bar graph comparing the mean placebo-adjusted 24-hour (trough) change in FEV1 (L) for the 200 µg dose of glycopyrrolate delivered via the high efficiency nebulizer to the 200 µg dose delivered via the conventional jet nebulizer, the high efficiency nebulizer provided significantly improved improvement in lung function at 24 hours post-administration of glycopyrrolate. This is the first known disclosure of a clinically meaningful improvement in lung function greater than 12 hours for any solution formulation of glycopyrrolate at any dose.

Figure 2:
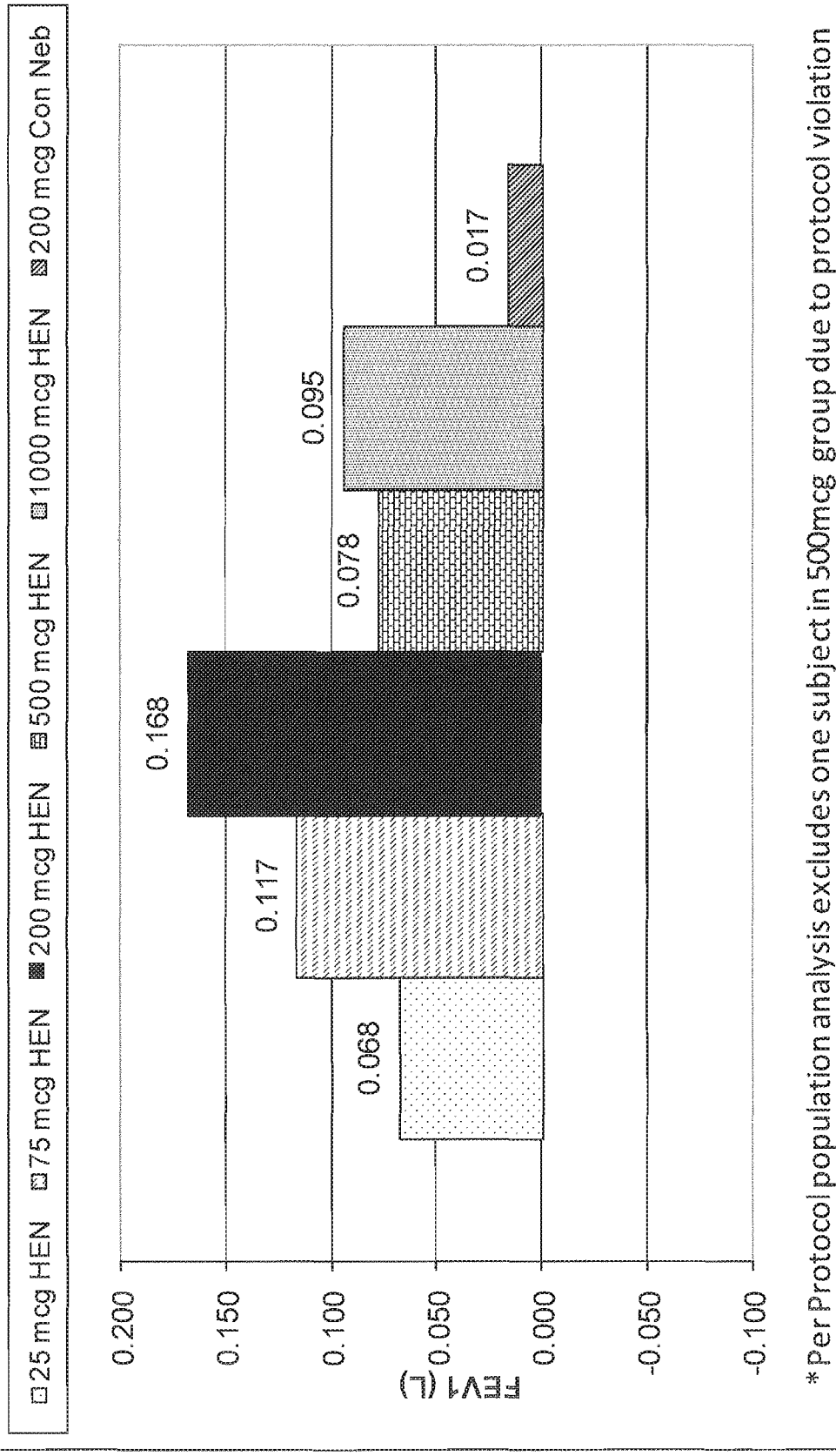
FIG. 2 is a graph comparing the placebo-adjusted 24-hour (trough) $FEV_1$ (L) obtained by administering 25 µg, 75 µg, 200 µg, 500 µg and 1000 µg of glycopyrrolate with a high efficiency nebulizer (left 5 bars) and 200 µg with a conventional jet nebulizer (right bar).

Administration of glycopyrrolate with a high efficiency nebulizer provides prolonged efficacy across a broad dosage range. As can be seen in FIG. 2, which is a graph comparing the mean placebo-adjusted 24-hour (trough) FEV1 (L) obtained by administering 25 µg, 75 µg, 200 µg, 500 µg and 1000 µg of glycopyrrolate with a high efficiency nebulizer (left 5 bars) and 200 µg with the conventional jet nebulizer (right bar), the high efficiency nebulizer provided significant improvement in lung function compared to baseline at 24 hours post-administration of glycopyrrolate for each of 75 µg, 200 µg, 500 µg and 1000 µg glycopyrrolate doses. There is no known teaching in the art that administration of a drug with a high efficiency nebulizer will result in greater duration of efficacy.

Figure 5:
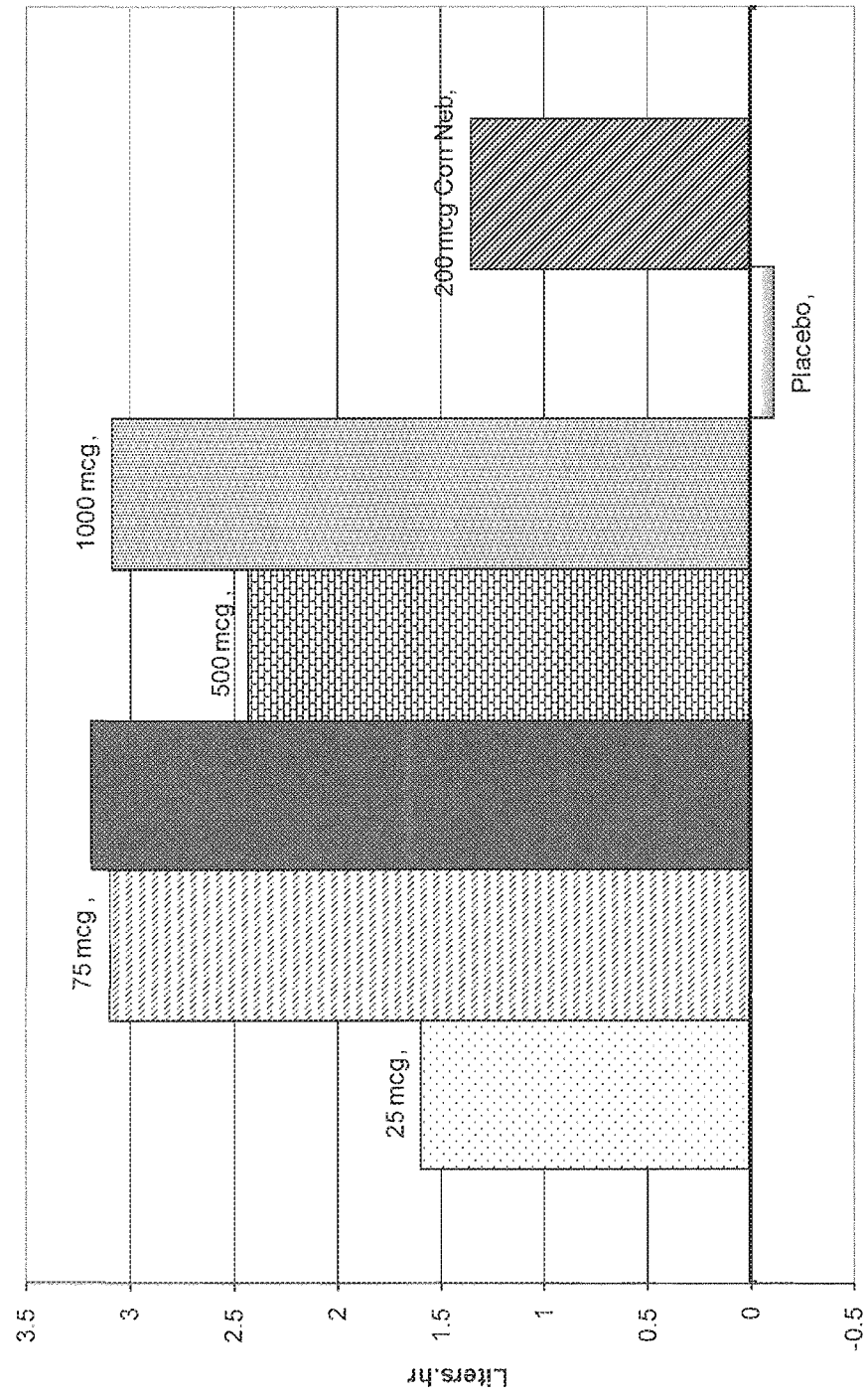
FIG. 5 is a graph comparing the area under the $FEV_1$ (L, above baseline) curve from 0-24 hours ($AUC_{0-24}$) obtained by administering 25 µg, 75 µg, 200 µg, 500 µg and 1000 µg of glycopyrrolate with a high efficiency nebulizer (left 5 bars); and placebo and 200 µg of glycopyrrolate with a conventional jet nebulizer (right 2 bars). The $AUC_{0-24}$ results are shown in L·hr.

Another measure of improved lung function is the baseline- and placebo-adjusted area under the $FEV_1$ change curve from 0-24 hours ($FEV_1 AUC_{0-24}$). FIG. 5 compares the area under the $FEV_1$ change (L, above baseline) curve from 0-24 hours ($FEV_1 AUC_{0-24}$) obtained by administering 25 µg, 75 µg, 200 µg, 500 µg and 1000 µg of glycopyrrolate with a high efficiency nebulizer (left 5 bars); and placebo and 200 µg of glycopyrrolate with the conventional jet nebulizer (right 2 bars). The $FEV_1 AUC_{0-24}$ results are shown in units of L·hr. As can be seen in FIG. 5, glycopyrrolate delivered with a high efficiency nebulizer produced significantly improved lung function over the period from 0-24 hours.

Figure 6:
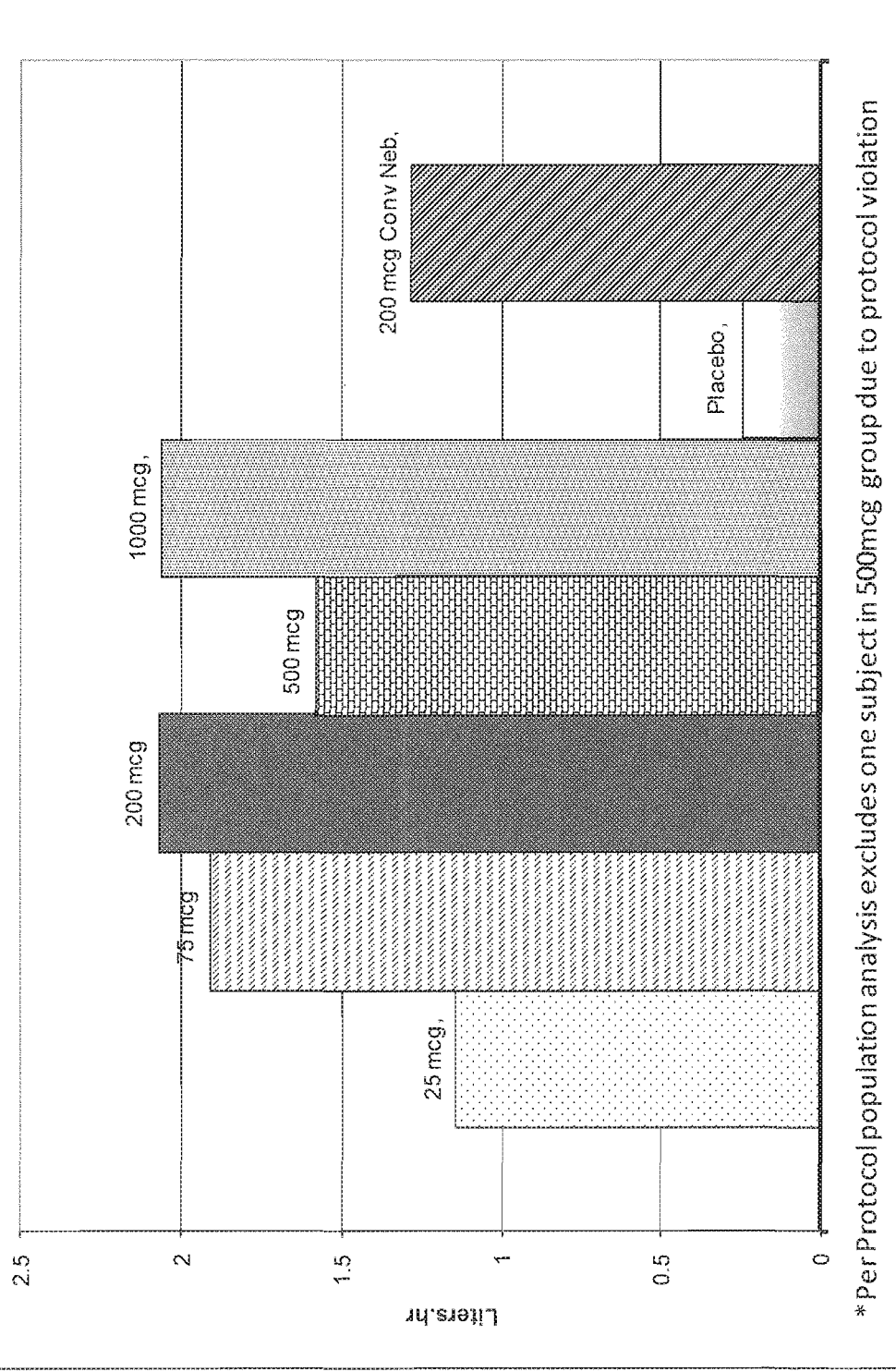
FIG. 6 is a graph comparing the area under the $FEV_1$ (L, above baseline) curve from 0-12 hours ($AUC_{0-12\ hrs}$) obtained by administering 25 µg, 75 µg, 200 µg, 500 µg and 1000 µg of glycopyrrolate with a high efficiency nebulizer (left 5 bars); and placebo and 200 of glycopyrrolate with a conventional jet nebulizer (right 2 bars). The $AUC_{0-12}$ results are shown in L·hr. The AUC values for the doses delivered by the high efficiency nebulizer achieved a similar robust magnitude of $FEV_1$ improvement as the dose delivered by the conventional jet nebulizer over the first 12 hours post-administration.

FIG. 6 is a graph comparing the area under the $FEV_1$ change (L, above baseline) curve from 0-12 hours ($AUC_{0-12\ hrs}$) obtained by administering 25 µg, 75 µg, 200 µg, 500 µg and 1000 µg of glycopyrrolate with a high efficiency nebulizer (left 5 bars); and placebo and 200 µg of glycopyrrolate with a conventional jet nebulizer (right 2 bars). The $AUC_{0-12}$ results are shown in L·hr. The $FEV_1$ AUC values for the 25 µg dose delivered by the high efficiency nebulizer achieved a similar robust magnitude of $FEV_1$ improvement as the dose delivered by the conventional jet nebulizer over the first 12 hours post-administration. The $FEV_1$ AUC values for the 75 µg, 200 µg, 500 µg and 1000 µg of glycopyrrolate delivered with a high efficiency nebulizer were significantly higher compared to the $FEV_1$ AUC value for the 200 µg dose delivered with the conventional jet nebulizer.

Figure 7:
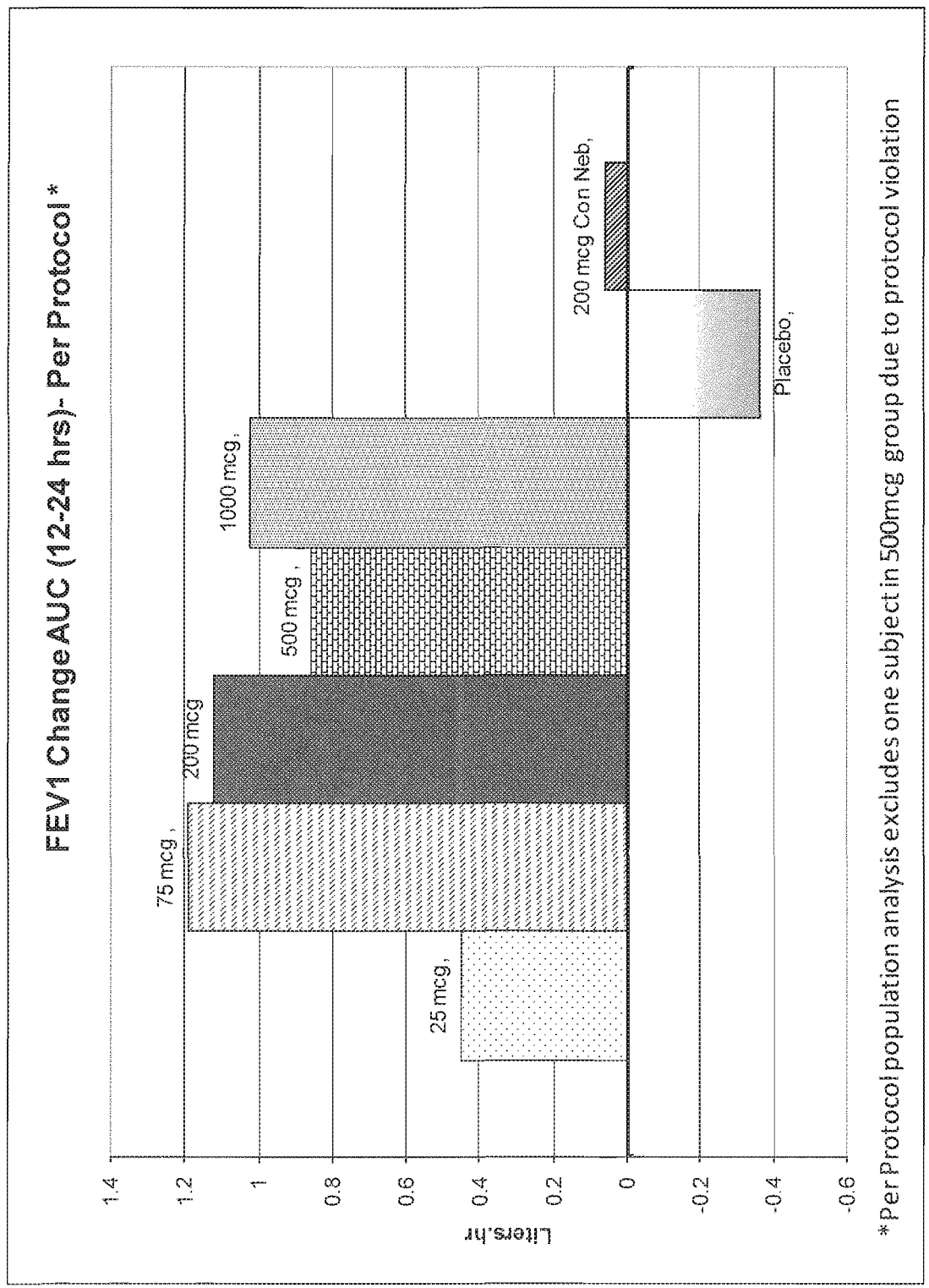
FIG. 7 is a graph comparing the area under the $FEV_1$ (L, above baseline) curve from 12-24 hours ($AUC_{12-24}$) obtained by administering 25 µg, 75 µg, 200 µg, 500 µg and 1000 µg of glycopyrrolate with a high efficiency nebulizer (left 5 bars); and placebo and 200 µg of glycopyrrolate with a conventional jet nebulizer (right 2 bars). The $AUC_{12-24}$ results are shown in L·hr. Although the subjects that received the 200 µg dose via a conventional nebulizer achieved similar AUC $FEV_1$ values from 0-24 hours, and 12-24 hours, as the AUC $FEV_1$ values achieved by those subjects who received the 25 µg dose administered by the high efficiency nebulizer, the mean AUC $FEV_1$ value for the $FEV_1$ response to the 200 µg dose via the conventional nebulizer was inferior and not clinically meaningful during 12-24 hours post-dosing, whereas all doses greater than 25 µg administered by the high efficiency nebulizer achieved robust prolonged duration of bronchodilation over the entire 24 hours.

The improved duration of therapeutic activity of glycopyrrolate administered with a high efficiency nebulizer, as compared to the conventional jet nebulizer, can best be observed in FIG. 7, which compares the area under the $FEV_1$ change (L, above baseline) curve from 12-24 hours ($AUC_{12-24}$) obtained by administering 25 µg, 75 µg, 200 µg, 500 µg and 1000 µg of glycopyrrolate with a high efficiency nebulizer (left 5 bars); and placebo and 200 µg of glycopyrrolate with a conventional jet nebulizer (right 2 bars). The $FEV_1$ $AUC_{12-24}$ results are shown in units of L·hr. As can be seen in FIG. 7, at every glycopyrrolate dose tested, the improvement in lung function with glycopyrrolate administered with a high efficiency nebulizer was significantly greater between 12 and 24 hours than with the dose of glycopyrrolate administered with the conventional jet nebulizer.

Figure 8:
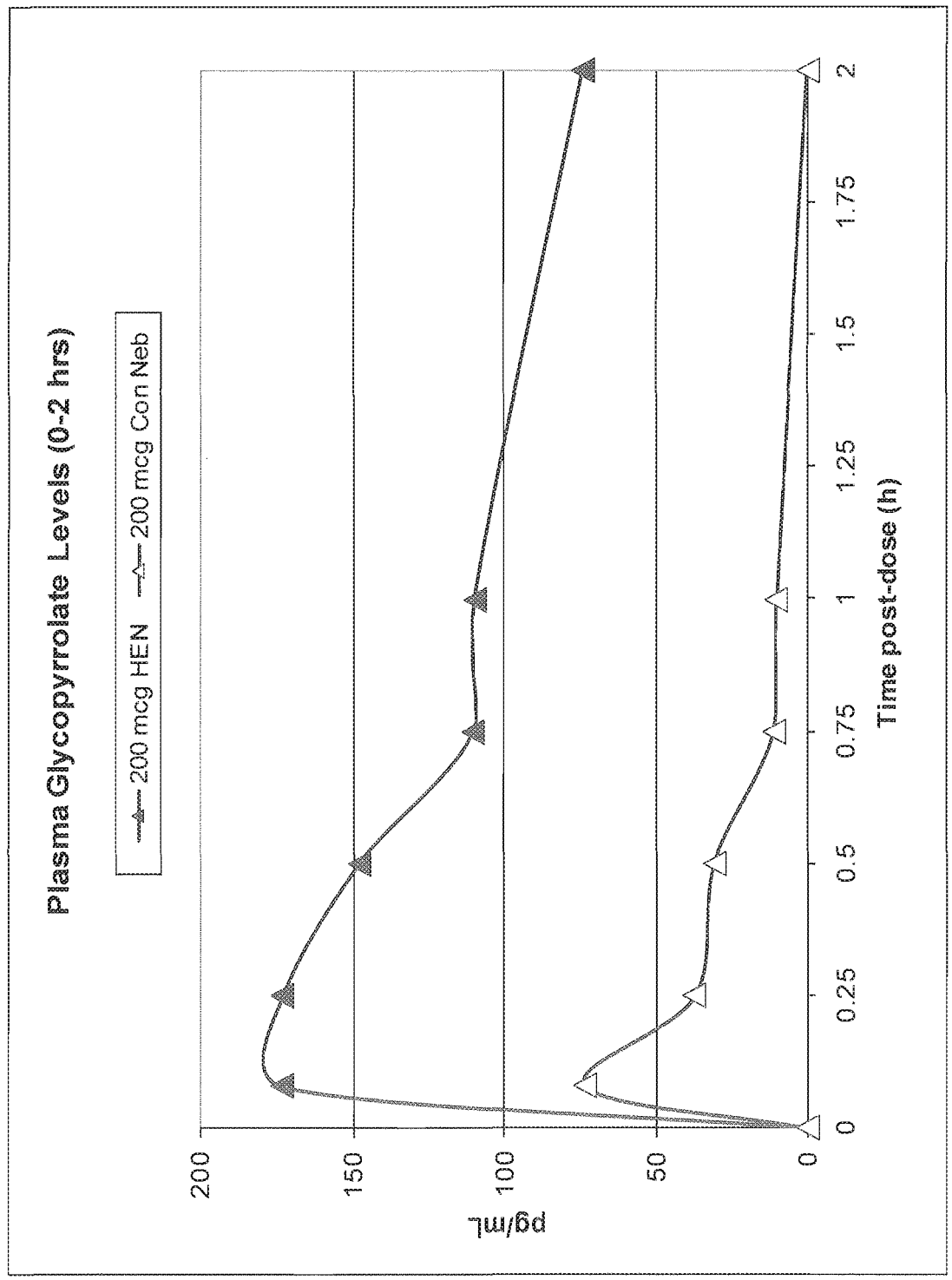
FIG. 8 is a line graph comparing glycopyrrolate blood plasma concentrations during the first two hours after administration of 200 µg glycopyrrolate with a high efficiency nebulizer (upper line) and 200 µg glycopyrrolate with a conventional jet nebulizer (lower line).

In order to better understand the mechanism by which administration of glycopyrrolate with a high efficiency nebulizer improves lung function, blood plasma concentration levels of glycopyrrolate were obtained for the 200 µg high efficiency nebulizer and 200 µg conventional nebulizer study arms. Table 1-3 summarizes the pharmacokinetic (PK) measurements obtained. FIG. 8 is a line graph comparing glycopyrrolate blood plasma concentrations during the first two hours after administration of 200 µg glycopyrrolate with a high efficiency nebulizer (upper line) and 200 µg glycopyrrolate with the conventional jet nebulizer (lower line). As can be seen in FIG. 8, in addition to exhibiting a later Tmax and a considerably higher Cmax, the high efficiency nebulizer (HEN) arm also exhibited significantly longer elimination. Without wishing to be bound by theory, it appears that this may be evidence of a depot effect, whereby the enhanced deposition of glycopyrrolate in the lungs, and particularly in the periphery of a diseased COPD lung which is characterized by poor mucociliary clearance, may result in prolonged duration of bronchodilation.

One property of administration of glycopyrrolate with a high efficiency nebulizer is an enhancement in glycopyrrolate blood plasma AUC relative to Cmax. As can be seen in Table 1-1, the ratio of AUC/Cmax for glycopyrrolate administered with a high efficiency nebulizer is much greater than the AUC/Cmax for glycopyrrolate administered with the conventional jet nebulizer. Achievement of a AUC/Cmax ratio greater than 0.5 hrs, or 1 hr, or 1.5 hrs, or 2 hrs in combination with a total $AUC_{0-t}$ greater than 100 pg/mL·h, or 200 pg/mL·h is believed to be important for achievement of a 24 hour duration of activity for a solution formulation of glycopyrrolate.

TABLE 1-1

PK Values for Administration of Glycopyrrolate with High Efficiency and Conventional Jet Nebulizers

| Pharmacokinetic Value | High Efficiency Nebulizer 200 µg | Conventional Nebulizer 200 µg |
|---|---|---|
| Cmax | 177 pg/mL | 76 pg/mL |
| Tmax | 11.6 min | 8.2 min |
| $AUC_{(0-t)}$ | 429 pg/mL · h | 26 pg/mL · h |
| $AUC_{(0-inf)}$ | 615 pg/mL · h | 70 pg/mL · h |
| $Cmax/AUC_{(0-t)}$ | 0.41/h | 2.92/h |
| $AUC_{(0-t)}/Cmax$ | 2.42 h | 0.35 h |
| $t^{1/2}$ | 4.1 h | 0.9 h |
| $t^{1/2}_{(0-60\ min)}$ | 72 min | 46 min |

As can be seen in Table 1.1, the Tmax is longer (about 12 min. vs about 8 min.) for glycopyrrolate when administered with the high efficiency nebulizer than with the conventional jet nebulizer, demonstrating a slower elimination of glycopyrrolate from the lung/airway compartment into the systemic blood when using the high efficiency nebulizer. Additional evidence of a slower elimination of glycopyrrolate from the lung/airway compartment when delivered by a high efficiency nebulizer is that, for the first 60 minutes post-dosing, the plasma elimination half-life of glycopyrrolate was much greater (prolonged) as compared to administration of the same dose with a conventional jet nebulizer (72 min. vs 46 min.).

Example 2: Randomized, Double-Blind, Placebo-Controlled Cross-Over, Single Dose Study At least about thirty (30) adult human COPD patients of ages >45 years are randomized to one of six treatment groups: (1) 25 µg glycopyrrolate administered with a high efficiency nebulizer; (2) 50 µg of glycopyrrolate administered with a high efficiency nebulizer; (3) 100 µg of glycopyrrolate administered with a high efficiency nebulizer; (4) 200 µg of glycopyrrolate administered with a high efficiency nebulizer; (5) 500 µg of glycopyrrolate administered with a high efficiency nebulizer; (6) placebo administered with a high efficiency nebulizer.

Lung function is determined by spirometry, which measures e.g. $FEV_1$ and other suitable spirometry parameters. Spirometry is conducted immediately before and at predetermined intervals following administration of the glycopyrrolate to the patients, Additionally, the patients will be monitored for any adverse events, as well as for vital signs and electrocardiogram.

A goal of this study is to verify that glycopyrrolate administered to human patients with a high efficiency nebulizer at the tested doses produces in a patient or population of patients a therapeutic effect (i.e. at least one spirometry measurement, e.g. through $FEV_1$, is at least 10% above baseline for a significant period of time, e.g. at least 24 hours.)

Another goal of this study is to verify that glycopyrrolate administered to human patients with a high efficiency nebulizer produces in a patient or population of patients a suitable adverse event profile.

Example 3: Aerosol Characterization of Glycopyrrolate Inhalation Solution in a High Efficiency Nebulizer and a Conventional Jet Nebulizer Objective The object of the study was to determine and compare the drug delivery efficiency of two different nebulizer systems, a high efficiency nebulizer and a conventional jet nebulizer, using a glycopyrrolate inhalation solution (GIS). Droplet size and respirable fraction of the aerosol were measured by laser diffraction, while delivered dose, nebulization time and nebulizer residue were assessed by breath simulation using a standard adult breathing pattern.

Summary

Two different nebulizers were characterized by laser diffraction and breath simulation. An innovative new vibrating membrane, high efficiency nebulizer (PARI eFlow® 30 L), and a commonly used conventional jet nebulizer (DeVilbiss 800 D). 12 laser diffraction and 12 breath simulation experiments in total were carried out. The parameters of DD, nebulization time, MMD, GSD, RD<5 µm and RDDR were determined upon these measurements.

The high efficiency nebulizer generated droplets of a mass median diameter (MMD) of around 3.5 µm and a geometric standard deviation (GSD) of 1.55 compared to the MMD and GSD obtained from the conventional jet nebulizer (3.6 µm, 2.94).

To determine the delivered dose (DD), breath simulator experiments were performed with an adult breathing pattern.

The respirable dose (RI)) is calculated by multiplying the DD, obtained in breath simulation experiments, by the percentage of aerosol particles less than 5 µm (RF<5 µm) determined by laser diffraction.

Materials and Methods

The drug formulation was a 2 mg/mL, glycopyrrolate solution (GIS). This solution was tested at the following quantities (mg) and volumes (mL): High efficiency nebulizer @1 mg/0.5 mL, and conventional jet nebulizer @, 4 mg/2 mL.

Breath simulation tests were conducted and a breath simulator with adult breathing pattern was conducted (500 mL tidal volumes, 15 breaths/min, inhalation/exhalation ratio 50:50).

The nebulizers were equipped with expiratory filters and connected via an inspiratory filter to the breathing simulator. The inspiratory filter was changed after the first minute, the second filter remained until the end of nebulization. The end of the nebulization was reached for the high efficiency nebulizer when the nebulizer switched off automatically; for the jet nebulizer, the end of nebulization was achieved one minute after sputtering began.

Laser diffraction was used to assess the geometric droplet size distribution with a Malvern MasterSizerX® laser diffraction measurement device, Airflow was 15 L/min±0.1 L/min; temperature was 23° C.±2° C.; relative humidity was 50% f 5%. The parameters obtained with laser diffraction were: mass median diameter of the droplets (MMD), respirable fraction (RF), geometric standard deviation (GSD), and total output rate (TOR).

The calculated parameters were respirable dose (RD) and respirable drug delivery rate (RDDR).

The results of this in vitro aerosol characterization are presented in Table 5-1.

TABLE 5-1

In vitro aerosol characterization of a high efficiency nebulizer and a conventional jet nebulizer.

| | High Efficiency Nebulizer | Conventional Jet Nebulizer |
|---|---|---|
| MMD/MMAD | 3.5 μm | 3.6 μm |
| GSD | 1.6 μm | 2.9 μm |
| DD | 66% | 11% |
| RF < 5 μm | 80% | 67% |
| RD < 5 μm | 52.6% | 7.5% |
| RDDR< 5 μm | 39% | 2% |

CONCLUSION

While preferred embodiments of the present invention have been shown and described herein, it will be obvious to those skilled in the art that such embodiments are provided by way of example only. Numerous variations, changes, and substitutions will now occur to those skilled in the art without departing from the invention. It should be understood that various alternatives to the embodiments of the invention described herein may be employed in practicing the invention. It is intended, that the following claims define the scope of the invention and that methods and structures within the scope of these claims and their equivalents be covered thereby.

What is claimed is:

1. A pharmaceutical composition, comprising an aqueous solution of glycopyrrolate having a volume of about 0.7 mL to about 1.0 mL, a glycopyrrolate concentration of about 25 μg/mL to about 400 μg/mL, and a pH of about 3 to about 5, wherein the solution is free of other bronchodilating agents and is substantially free of preservatives.

2. The pharmaceutical composition of claim 1, further comprising an organic acid.

3. The pharmaceutical composition of claim 2, wherein the organic acid is citric acid or a pharmaceutically acceptable salt thereof.

4. The pharmaceutical composition of claim 1, wherein the solution is substantially free of benzyl alcohol.

5. The pharmaceutical composition of claim 1, wherein the glycopyrrolate concentration is about 25 μg/mL.

6. The pharmaceutical composition of claim 1, wherein the volume is about 1 mL.

7. The pharmaceutical composition of claim 1, wherein the pharmaceutical composition is contained in a single dose ampule.

8. The pharmaceutical composition of claim 1, comprising an aqueous solution of glycopyrrolate having a volume of about 1.0 mL, a glycopyrrolate concentration of about 25 μg/mL, and a pH of about 3 to about 5, wherein the solution is free of other bronchodilating agents and is substantially free of preservatives.

9. The pharmaceutical composition of claim 8, wherein said aqueous solution further comprises citric acid or a pharmaceutically acceptable salt thereof.

10. A method of treating chronic obstructive pulmonary disease (COPD) in a subject comprising administering to the subject a pharmaceutical composition via a high efficiency nebulizer, wherein the pharmaceutical composition comprises an aqueous solution of glycopyrrolate having a volume of about 0.7 mL to about 1.0 mL, a glycopyrrolate concentration of about 25 μg/mL to about 400 μg/mL, and a pH of about 3 to about 5, wherein the solution is free of other bronchodilating agents and is substantially free of preservatives.

11. The method of claim 10, wherein the pharmaceutical composition further comprises an organic acid.

12. The method of claim 11, wherein the organic acid is citric acid or a pharmaceutically acceptable salt thereof.

13. The method of claim 10, wherein the solution is substantially free of benzyl alcohol.

14. The method of claim 10, wherein the glycopyrrolate concentration is about 25 μg/mL.

15. The method of claim 10, wherein the volume is about 1 mL.

16. The method of claim 10, wherein the pharmaceutical composition is contained in a single dose ampule.

17. The method of claim 10, wherein the pharmaceutical composition comprises an aqueous solution of glycopyrrolate having a volume of about 1.0 mL, a glycopyrrolate concentration of about 25 μg/mL, and a pH of about 3 to about 5, wherein the solution is free of other bronchodilating agents and is substantially free of preservatives.

18. The method of claim 17, wherein said aqueous solution further comprises citric acid or a pharmaceutically acceptable salt thereof.

* * * * *